(12) United States Patent
DeVita et al.

(10) Patent No.: US 7,652,058 B2
(45) Date of Patent: Jan. 26, 2010

(54) OCTAHYDROPYRANO[3,4-C]PYRROLE TACHYKININ RECEPTOR ANTAGONISTS

(75) Inventors: Robert J. DeVita, Westfield, NJ (US); Jinlong Jiang, Scotch Plains, NJ (US); Sander G. Mills, Scotch Plains, NJ (US); Jonathan R. Young, Southborough, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 400 days.

(21) Appl. No.: 11/792,514

(22) PCT Filed: Dec. 12, 2005

(86) PCT No.: PCT/US2005/044822

§ 371 (c)(1),
(2), (4) Date: Jun. 6, 2007

(87) PCT Pub. No.: WO2006/065711

PCT Pub. Date: Jun. 22, 2006

(65) Prior Publication Data

US 2008/0108689 A1 May 8, 2008

Related U.S. Application Data

(60) Provisional application No. 60/635,777, filed on Dec. 14, 2004.

(51) Int. Cl.
*A61K 31/407* (2006.01)
*C07D 491/052* (2006.01)
(52) U.S. Cl. ...................... 514/414; 548/453
(58) Field of Classification Search ...................... None
See application file for complete search history.

(56) References Cited

U.S. PATENT DOCUMENTS 4,535,169 A    8/1985   Krstenansky et al.

FOREIGN PATENT DOCUMENTS

WO    WO9714671 A1    4/1997
WO    WO2005073191 A1    8/2005

*Primary Examiner*—Kamal A Saeed
(74) *Attorney, Agent, or Firm*—Yong Zhao; Valerie J. Camara

(57) ABSTRACT

The present invention is directed to certain hydropyranopyrrolidine compounds which are useful as neurokinin-1 (NK-1) receptor antagonists, and inhibitors of tachykinin and in particular substance P. The invention is also concerned with pharmaceutical formations comprising these compounds as active ingredients and the use of the compounds and their formulations in the treatment of certain disorders, including emesis, urinary incontinence, depression, and anxiety.

12 Claims, No Drawings

OCTAHYDROPYRANO[3,4-C]PYRROLE TACHYKININ RECEPTOR ANTAGONISTS

CROSS REFERENCE TO RELATED APPLICATIONS

This application is a U.S. National Phase application under 35 U.S.C. §371 of PCT Application No. PCT/US2005/044822, filed Dec. 12, 2005, which claims priority under 35 U.S.C. §119(e) from U.S. Provisional Application Ser. No. 60/635,777, filed Dec. 14, 2004.

BACKGROUND OF THE INVENTION

Substance P is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence. In addition to substance P, the known mammalian tachykinins include neurokinin A and neurokinin B. The current nomenclature designates the receptors for substance P, neurokinin A, and neurokinin B as neurokinin-1 (NK-1), neurokinin-2 (NK-2), and neurokinin-3 (NK-3), respectively.

Tachykinin, and in particular substance P, antagonists are useful in the treatment of clinical conditions which are characterized by the presence of an excess of tachykinin, in particular substance P, activity, including disorders of the central nervous system, nociception and pain, gastrointestinal disorders, disorders of bladder function and respiratory diseases.

SUMMARY OF THE INVENTION

The present invention is directed to certain hydropyranopyrrole compounds which are useful as neurokinin-1 (NK-1) receptor antagonists, and inhibitors of tachykinin and in particular substance P. The invention is also concerned with pharmaceutical formulations comprising these compounds as active ingredients and the use of the compounds and their formulations in the treatment of certain disorders, including emesis, urinary incontinence, depression, and anxiety.

DETAILED DESCRIPTION OF THE INVENTION

The present invention is directed to compounds of the formula I:

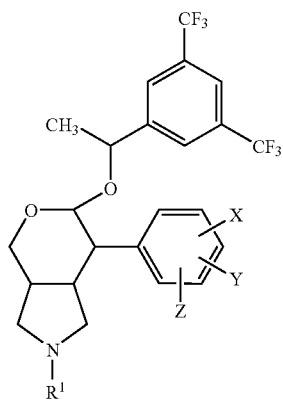

wherein:

$R^1$ is selected from the group consisting of:
(1) hydrogen,
(2) $C_{1-6}$alkyl, which is unsubstituted or substituted with halogen, hydroxyl or phenyl,
(3) cyclopentenone, which is unsubstituted or substituted with hydroxyl or methyl,
(4) furanone, which is unsubstituted or substituted with methyl,
(5) —(CO)—$C_{1-6}$alkyl,
(6) —(CO)—$NH_2$,
(7) —(CO)—$NHC_{1-6}$alkyl, and
(8) —(CO)—$N(C_{1-6}alkyl)(C_{1-6}alkyl)$;

X, Y and Z are independently selected from the group consisting of:
(1) hydrogen,
(2) halo, and
(3) methyl;

and pharmaceutically acceptable salts thereof and individual enantiomers and diastereomers thereof.

An embodiment of the present invention includes compounds of the formula Ia:

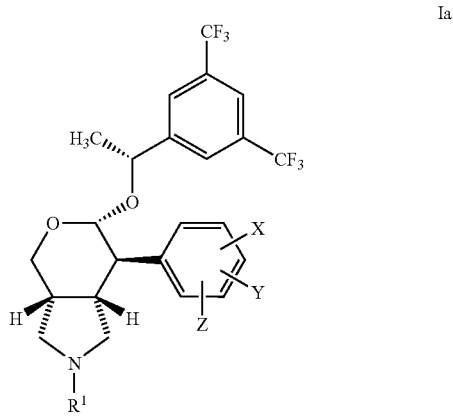

wherein $R^1$ and X, Y and Z are defined herein;

and pharmaceutically acceptable salts thereof and individual enantiomers and diastereomers thereof.

An embodiment of the present invention includes compounds of the formula Ib:

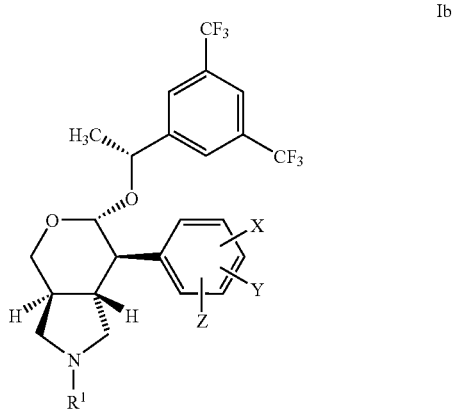

wherein R¹ and X, Y and Z are defined herein;
and pharmaceutically acceptable salts thereof and individual enantiomers and diastereomers thereof.

An embodiment of the present invention includes compounds wherein R¹ is selected from the group consisting of:
(1) hydrogen,
(2) $C_{1-3}$alkyl, which is unsubstituted or substituted with hydroxyl or phenyl,
(3) cyclopent-2-en-1-one, which is unsubstituted or substituted with hydroxyl or methyl,
(4) furanone, which is unsubstituted or substituted with methyl,
(5) —(CO)—$C_{1-3}$alkyl,
(6) —(CO)—$NH_2$,
(7) —(CO)—$NHC_{1-3}$alkyl, and
(8) —(CO)—$N(C_{1-3}$alkyl)($C_{1-3}$alkyl).

Within this embodiment the present invention includes compounds wherein R¹ is selected from the group consisting of:
(1) hydrogen,
(2) methyl,
(3) 2-phenylethyl,
(4) 2-hydroxyethyl,
(5) cyclopent-2-en-1-one,
(6) 5-hydroxycyclopent-2-en-1-one,
(7) 4-hydroxycyclopent-2-en-1-one,
(8) 2-methylcyclopent-2-en-1-one,
(9) 5-furanone,
(10) acetyl,
(11) acetamido,
(12) methyl-acetamido, and
(13) dimethyl-acetamido.

Further within this embodiment, the present invention is directed to compounds wherein R¹ is hydrogen.

Also further within this embodiment, the present invention is directed to compounds wherein R¹ is methyl, 2-phenylethyl or 2-hydroxyethyl.

Also further within this embodiment, the present invention is directed to compounds wherein R¹ is:

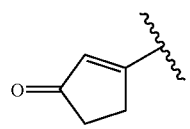

which is unsubstituted or substituted with hydroxyl or methyl.

Also further within this embodiment, the present invention is directed to compounds wherein R¹ is:

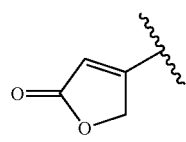

which is unsubstituted or substituted with methyl.

Also further within this embodiment, the present invention is directed to compounds wherein R¹ is acetyl, acetamido, methyl-acetamido or dimethyl-acetamido.

An embodiment of the present invention includes compounds wherein X, Y and Z are hydrogen. An embodiment of the present invention includes compounds wherein X is fluorine, Y is hydrogen, and Z is hydrogen. An embodiment of the present invention includes compounds wherein X is 4-fluoro, Y is hydrogen, and Z is hydrogen. An embodiment of the present invention includes compounds wherein X is methyl, Y is hydrogen, and Z is hydrogen. An embodiment of the present invention includes compounds wherein X is 2-methyl, Y is hydrogen, and Z is hydrogen.

Specific embodiments of the present invention include a compound which is selected from the group consisting of the subject compounds of the Examples herein and pharmaceutically acceptable salts thereof and individual enantiomers and diastereomers thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

There are several acceptable methods of naming the compounds discussed herein.

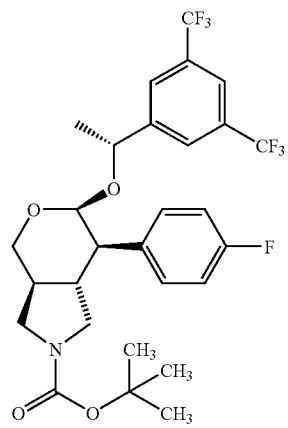

For example, the above compound can be named either as "(3aS,6S,7R,7aR) tert-butyl-6-{(1R)-1-[3,5-bis(trifluoromethyl)phenyl]ethoxy}-7-(4-fluorophenyl)hexahydropyrano[3,4-c]pyrrole-2(3H)-carboxylate" or "tert-butyl(3aS,6S,7R,7aR)-6-{(1R)-1-[3,5-bis(trifluoromethyl)phenyl]ethoxy}-7-(4-fluorophenyl)hexahydropyrano[3,4-c]pyrrole-2(3H)-carboxylate. The core structure may be generally referred to as octahydropyranopyrrole, hexahydropyranopyrrolidine, perhydropyranopyrrole, hydropyranopyrrolidine, or hydropyranopyrrole compounds.

As appreciated by those of skill in the art, halo or halogen as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The compounds of the present invention are useful in the prevention and treatment of a wide variety of clinical conditions which are characterized by the presence of an excess of tachykinin, in particular substance P, activity. Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculoskeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis. Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastroesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia, frequent urination and urinary incontinence, including the prevention or treatment of overactive bladder with symptoms of urge urinary incontinence, urgency, and frequency; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine. The compounds of the present invention are also of value in the treatment of a combination of the above conditions, in particular in the treatment of combined post-operative pain and post-operative nausea and vomiting.

The compounds of the present invention are particularly useful in the prevention or treatment of emesis, including acute, delayed or anticipatory emesis, such as emesis induced by chemotherapy, radiation, toxins, pregnancy, vestibular disorders, motion, surgery, migraine, and variations in intercranial pressure. For example, the compounds of the present invention are of use optionally in combination with other antiemetic agents for the prevention of acute and delayed nausea and vomiting associated with initial and repeat courses of moderate or highly emetogenic cancer chemotherapy, including high-dose cisplatin. Most especially, the compounds of the present invention are of use in the treatment of emesis induced by antineoplastic (cytotoxic) agents, including those routinely used in cancer chemotherapy, and emesis induced by other pharmacological agents, for example, rolipram. Examples of such chemotherapeutic agents include alkylating agents, for example, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics. Particular examples of chemotherapeutic agents are described, for instance, by D. J. Stewart in Nausea and Vomiting: Recent Research and Clinical Advances, Eds. J. Kucharczyk et al, CRC Press Inc., Boca Raton, Fla., USA (1991) pages 77-203, especially page 188. Commonly used chemotherapeutic agents include cisplatin, dacarbazine (DTIC), dactinomycin, mechlorethamine, streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in Cancer Treatment Reports (1984) 68(1), 163-172]. A further aspect of the present invention comprises the use of a compound of the present invention for achieving a chronobiologic (circadian rhythm phase-shifting) effect and alleviating circadian rhythm disorders in a mammal. The present invention is further directed to the use of a compound of the present invention for blocking the phase-shifting effects of light in a mammal.

The present invention is further directed to the use of a compound of the present invention or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of the present invention or a pharmaceutically acceptable salt thereof. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus, fibromyalgia, muscle pain, sleep apnea and restless legs and non specific REM disturbances as seen in ageing.

The particularly preferred embodiments of the instant invention are the treatment of emesis, urinary incontinence, depression or anxiety by administration of the compounds of the present invention to a subject (human or animal) in need of such treatment.

The present invention is directed to a method for the manufacture of a medicament for antagonizing the effect of substance P at its receptor site or for the blockade of neurokinin-1 receptors in a mammal comprising combining a compound of the present invention with a pharmaceutical carrier or diluent. The present invention is further directed to a method for the manufacture of a medicament for the treatment of a physiological disorder associated with an excess of tachykinins in a mammal comprising combining a compound of the present invention with a pharmaceutical carrier or diluent.

The present invention also provides a method for the treatment or prevention of physiological disorders associated with an excess of tachykinins, especially substance P, which method comprises administration to a patient in need thereof of a tachykinin reducing amount of a compound of the present invention or a composition comprising a compound of the present invention. As used herein, the term "treatment" or "to treat" refers to the administration of the compounds of the present invention to reduce, ameliorate, or eliminate either the symptoms or underlying cause of the noted disease conditions, in a subject (human or animal) that suffers from that condition or displays clinical indicators thereof. The term "prevention" or "to prevent" refers to the administration of the compounds of the present invention to reduce, ameliorate, or eliminate the risk or likelihood of occurrence of the noted disease conditions, in a subject (human or animal) susceptible or predisposed to that condition.

The compounds of this invention are useful for antagonizing tachykinins, in particular substance P in the treatment of gastrointestinal disorders, central nervous system disorders, inflammatory diseases, pain or migraine and asthma in a mammal in need of such treatment. This activity can be demonstrated by the following assays.

Receptor Expression in COS: To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the assay.

Stable Expression in CHO: To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer supplemented with 0.625 mg/ml Herring sperm DNA at 300 V and 950 uF using the IBI GENEZAPPER (IBI). The transfected cells were incubated in CHO media [10% fetal calf serum, 100 U/ml penicillin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

Assay Protocol using COS or CHO: The binding assay of human NK1R expressed in either COS or CHO cells is based on the use of $^{125}$I-substance P ($^{125}$I-SP from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter. The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1 N HCl is added. Each well is sonicated at 4° C. and extracted with $CHCl_3$/methanol (1:1). The aqueous phase is applied to a 1 ml Dowex AG 1×8 ion exchange column. The column is washed with 0.1 N formic acid followed by 0.025 M ammonium formate-0.1 N formic acid. The inositol monophosphate is eluted with 0.2 M ammonium formate-0.1 N formic acid and quantitated by beta counter. In particular, the intrinsic tachykinin receptor antagonist activities of the compounds of the present invention may be demonstrated by these assays. The compounds of the following examples have activity in the aforementioned assays in the range of 0.05 nM to 10 □M. The activity of the present compounds may also be demonstrated by the assay disclosed by Lei, et al., *British J. Pharmacol.*, 105, 261-262 (1992).

According to a further or alternative aspect, the present invention provides a compound of the present invention for use as a composition that may be administered to a subject in need of a reduction of the amount of tachykinin or substance P in their body.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleageneous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The compositions containing compounds of the present invention may be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples in the pharmacy arts of unit dosage forms. The compositions containing compounds of the present invention may also be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individuals body in a therapeutically useful form and therapeutically effective amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories. The term "therapeutically effective amount" refers to a sufficient quantity of the compounds of the present invention, in a suitable composition, and in a suitable dosage form to treat or prevent the noted disease conditions.

The compounds of the present invention may be administered in combination with another substance that has a complimentary effect to the tachykinin and substance P inhibitors of the present invention. Accordingly, in the prevention or treatment of emesis, a compound of the present invention may be used in conjunction with other anti-emetic agents, especially $5HT_3$ receptor antagonists, such as ondansetron, granisetron, tropisetron, palenosetron and zatisetron, a corticosteroid, such as dexamethasone, or $GABA_B$ receptor agonists, such as baclofen. Likewise, for the prevention or treatment of migraine a compound of the present invention may be used in conjunction with other anti-migraine agents, such as ergotamines or $5HT_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), α-adrenoreceptor antagonists, atypical anti-depressants, benzodiazepines, $5-HT_{1A}$ agonists or antagonists, especially $5-HT_{1A}$ partial agonists, corticotropin releasing factor (CRF) antagonists, and pharmaceutically acceptable salts thereof. For the treatment or prevention of eating disorders, including obesity, bulimia nervosa and compulsive eating disorders, a compound of the present invention may be used in conjunction with other anorectic agents. It will be appreciated that for the treatment or prevention of pain or nociception or inflammatory diseases, a compound of the present invention may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent.

It will be appreciated that when using any combination described herein, both the compound of the present invention and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds. By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The compounds of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of the conditions associated with an excess of tachykinins, a suitable dosage level of the compounds of the present invention, or pharmaceutically acceptable salts thereof, is about 0.001 to 50 mg/kg per day, in particular about 0.01 to about 25 mg/kg, such as from about 0.05 to about 10 mg/kg per day. The dosage range will generally be about 0.5 to 1000 mg per patient per day, which may be administered in single or multiple doses. Preferably, the dosage range will be about 0.5 mg to 500 mg per patient per day; more preferably about 0.5 mg to 200 mg per patient per day; and even more preferably about 5 mg to 50 mg per patient per day. Specific dosages of the compounds of the present invention, or pharmaceutically acceptable salts thereof, for administration include 1 mg, 5 mg, 10 mg, 30 mg, 100 mg, and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions for treatment or prevention of excess tachykinins comprise about 1 mg, 5 mg, 10 mg, 30 mg, 100 mg, and 500 mg of active ingredient.

Several methods for preparing the compounds of this invention are illustrated in the following Examples. Starting materials and the requisite intermediates are in some cases commercially available, or can be prepared according to literature procedures or as illustrated herein. All $^1$H NMR spectra were obtained on instrumentation at a field strength of 400 or 500 MHz.

The following examples are provided for the purpose of further illustration only and are not intended to be limitations on the disclosed invention.

EXAMPLE 1

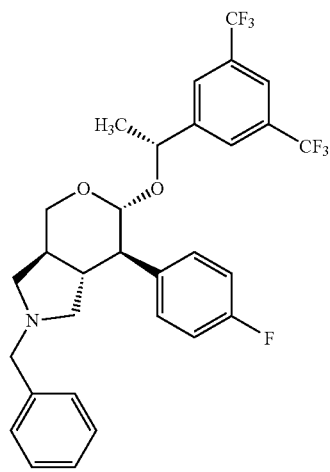

(3aS,6R,7R,7aR)-2-Benzyl-6-{(1R)-1-[3,5-bis(trifluoromethyl)phenyl]ethoxy}-7-(4-fluorophenyl)octahydropyrano[3,4-c]pyrrole Step A: Dimethyl[2-(benzaloxy)ethylidene]malonate To a solution of 76 mL dimethyl malonate (88 g, 0.67 mol) in 1.35 L dichloromethane in a round bottom flask, equipped with a septa, addition funnel stir bar and a nitrogen inlet was cooled to 2.5° C. in an ice bath. To the cooled solution, was added by addition funnel 0.67 L (0.67 mol) of a 1 M solution of TiCl$_4$ in dichloromethane at a rate of 5 mL/min (slight exotherm to 3.5° C.)., The resulting mixture was stirred with cooling for 30 min, then 93.5 mL (100 grams, 0.67 mol) benzyloxyacetaldehyde was added by syringe. The reaction mixture was stirred for 10 min. in an ice bath then 107.6 mL pyridine (105 g, 1.33 mol) was then added dropwise (slight exotherm to 4.5° C.). The reaction was allowed to warm gradually to RT overnight. The reaction mixture was poured over 4 kg of ice, extracted with 4LEtOAc, washed organic layer with brine, dried over MgSO4, filtered on a fritted funnel, and concentrated in vacuo. The crude residue was purified on silica gel (5 to 25% EtOAc/heptane using a gradient elution). This provided the title compound. $^1$H-NMR (CDCl$_3$): δ 3.78 (s, 3H), 3.83 (s, 3H), 4.41 (d, 2H, J=4.5 Hz), 4.58 (2, 2H), 7.19 (t, 1H, J=4.5 Hz), 7.25-7.35 (m, 5H) ppm.

Step B: 1-[(4-Fluorophenyl)acetyl]piperidine

4-Fluorophenylacetic acid (280 g, 1.82 mol) was suspended in 1.9 L toluene followed by the careful addition of 185 mL thionyl chloride (303 g, 2.545 mol). The reaction was heated to 105° C. for 16 hr (overnight). The reaction was allowed to cool to room temperature and the volatiles were removed in vacuo. The crude acid chloride was dissolved in 1.9 L THF, cooled to 0° C., and 0.72 L piperidine (618 g, 7.27 mol) was added. The reaction vessel was allowed to warm to ambient temperature for 18 hr. The mixture was quenched with a saturated solution of aq. NaHCO$_3$ and extracted several times with EtOAc. The combined organic extracts were washed with brine, dried over $Na_2SO_4$, and filtered on a fritted funnel. The volatiles were removed in vacuo and the crude residue was purified on silica gel and eluted with a mixture of EtOAc/heptanes (0-75% gradient elution). This furnished the title compound. $^1$H-NMR (CDCl$_3$): δ 1.32-1.42 (m, 2H), 1.48-1.64 (m, 4H), 3.34-3.42 (m, 2H), 3.54-3.60 (m, 2H), 3.69 (s, 2H), 6.90-7.05 (m, 2H), 7.18-7.24 (m, 2H) ppm.

Step C: Dimethyl[1-[(benzyloxy)methyl]-2-(4-fluorophenyl)-3-oxo-3-piperidin-1-ylpropyl]malonate The intermediate from example 1 step B (330 g, 1.5 mol) was dissolved in 7.2 L THF and cooled to –78° C. followed by the dropwise addition 1.8 L (1.8 mol) of a 1 M solution of LHMDS. The mixture was maintained at this temperature for 1.5 hr after which time a solution of the intermediate from example 1 step A (435.6 g, 1.65 mol) in 800 mL THF was added slowly. The reaction mixture was maintained at –78° C. for 1 hr. The reaction was quenched with 2 L saturated aqueous solution of ammonium chloride and warmed to ambient temperature. The aqueous mixture was extracted several times with EtOAc (4×2 L). The combined organic extracts were washed with brine, dried over $Na_2SO_4$, and filtered through a fritted funnel. The volatiles were removed in vacuo and the crude residue was purified on silica gel eluting with a mixture of t-butylmethylether/dichloromethane (0-7% gradient elution) to afford the title compound as a mixture of syn and anti isomers. On small scale chromatography, the first component eluted off the column (A) was identified as the anti isomer and the second component (B) was the syn isomer.

Step D: 2-syn-[1-[(Benzyloxy)methyl]-2-(4-fluorophenyl)-3-oxo-3-piperidin-1-ylpropyl]propane-1,3-diol The intermediate from example 1 step C (450 g, 929 mmol) was dissolved in 10 L THF and cooled to 0° C. Lithium borohydride (201.6 g, 9.29 mol) was added in a single portion. After stirring 30 minutes at 0° C., the reaction was warmed to ambient temperature where it was maintained for 16 hr (overnight). The reaction was cooled to 0° C. and another 5 equiv lithium borohydride (100.8 g, 4.645 mol) was added in a single portion. After stirring 30 minutes at 0° C., the reaction was warmed to ambient temperature where it was maintained for 16 hr (overnight). The reaction was cooled to 0° C., cautiously quenched with a saturated solution of ammonium chloride and warmed to ambient temperature for 1 hr. The aqueous solution was extracted with EtOAc (3×2 L). The combined organic fractions were washed with brine, dried over $Na_2SO_4$, and filtered through a fritted funnel. The volatiles were removed in vacuo and the crude residue was purified on silica gel and eluted first with a mixture of EtOAc/dichloromethane (10-90% gradient elution, 8 L) then 10% MeOH/dichloromethane (16 L). This provided the less polar anti isomer (A) and the syn title compound (B). $^1$H-NMR (CD$_3$OD) syn compound B: ☐ 0.90-1.15 (m, 1H), 1.25-1.40 (m, 1H), 1.42-1.65 (m, 4H), 1.95-1.05 (M, 1H), 2.74-2.82 (m, 1H), 3.00-3.03 (m, 1H), 3.30-3.42 (m, 1H), 3.42-3.75 (m, 7H), 3.78-3.84 (m, 1H), 4.19 (m, 2H), 4.40 (d, 1H, J=11.5 Hz), 7.00-7.15 (m, 2H), 7.20-7.40 (m, 7H) ppm.

Step E: racemic (3R,4R,5S and 3S,4S,5R)-4-[(benzyloxy)methyl]-3-(4-fluorophenyl)-5-(hydroxymethyl)tetrahydro-2H-pyran-2-one The syn intermediate from example 1 step D (157 g, 366 mmol) was dissolved in 4.7 L toluene followed by the dropwise addition of methanesulfonic acid (52.7 g, 549 mmol). The reaction mixture was maintained at ambient temperature for 18 hr. The reaction was quenched with a saturated solution of $Na_2CO_3$ and extracted with EtOAc (6×1 L). The combined organic extracts were washed with brine, dried over $Na_2SO_4$, filtered through a fritted funnel and concentrated in vacuo. The crude residue precipitated upon standing and was subsequently triturated with diethyl ether. The white precipitate was collected by filtration to provide the title compound. $^1$H-NMR (CD$_3$OD): δ 2.17-2.25 (m, 1H), 2.49 (dddd, 1H, J=6.0, 6.0, 12.0, 12.0 Hz), 3.11 (dd, 1H, J=3.0, 9.5 Hz), 3.27 (dd, 1H, J=2.5, 9.5 Hz), 3.62 (dd, 1H, J=6.5, 11.0 Hz), 3.67 (dd, J=5.0, 11.0 Hz), 4.18 (d, 1H, J=8.5 Hz), 4.35 (dd, 1H, J=11.5, 11.5 Hz), 4.42 (d, 1H, J=12.0 Hz), 4.45 (d, 1H, J=12.0 Hz), 4.49 (dd, 1H, J=6.0, 11.5 Hz), 7.01 (dd, 2H, J=9 Hz), 7.25-7.37 (m, 5H), 7.44 (dd, 2H, J=5.5, 9.0 Hz) ppm.

Step F: Racemic-(2S,3R,4R,5S and 2R,3S,4S,5R)-4-[(benzyloxy)methyl]-3-(4-fluorophenyl)-5-(hydroxymethyl)tetrahydro-2H-pyran-2-ol The intermediate from example 1 step E (6.85 g, 19.9 mmol) was dissolved in 200 mL DCM and cooled to –78° C. A 1.0 M solution of DIBAL-H (in toluene) was added dropwise over 20 minutes. The reaction was maintained at –78° C. for 90 minutes after which time a saturated aqueous solution of Rochelles salt was added. The reaction mixture was warmed to ambient temperature for 2 hr. Celite and 1 M HCl was added and stirred vigorously for an additional 45 minutes after which the mixture was filtered through a fritted funnel. The mixture was extracted twice with DCM. The combined extracts were dried over $Na_2SO_4$, filtered through a fritted funnel and concentrated in vacuo. This resulted in low recovery of the hemiacetal product. The celite and the aqueous layer were combined and a 1:1 mixture of methanol/EtOAc was added and the mixture was stirred overnight. This mixture was filtered on a fritted funnel, concentrated in vacuo, and diluted with EtOAc. The solution was washed with a saturated solution of $Na_2CO_3$, brine, dried over $Na_2SO_4$, filtered through a fritted funnel and concentrated in vacuo. This provided the final product. $^1$H-NMR (CD$_3$OD): δ 1.86-1.96 (m, 1H), 2.00-2.14 (m, 1H), 2.76 (dd, 1H, J=9.5, 11 Hz), 2.96 (dd, 1H, J=3.0, 10.0 Hz), 3.38-3.48 (m, 1H), 3.50 (dd, 1H, J=7.0, 11.5 Hz), 3.62 (dd, 1H, J=11.5, 11.5 Hz), 3.73 (dd, 1H, J=3.0, 11.5 Hz), 4.15 (dd, 1H, J=4.5, 11.5 Hz), 4.29 (d, 1H, J=12.5 Hz), 4.34 (d, 1H, J=12.5 Hz), 4.74 (d, 1H, J=9.0 Hz), 6.99 (dd, 2H, J=9.0, 9.0 Hz), 7.15-7.35 (m, 7H) ppm.

Step G: Racemic-(2R,3R,4R,5R and 2S,3S,4S,5S)-4-[(benzyloxy)methyl]-3-(4-fluorophenyl)-5-{[(4-nitrobenzoyl)oxy]methyl}tetrahydro-2H-pyran-2-yl 4-nitrobenzoate The intermediate from example 1 step F (6.44 g, 18.6 mmol) was dissolved in 200 mL DCM and cooled 0° C. followed by the addition of DMAP (0.23 g, 1.86 mmol), triethylamine (7.53 g, 74.4 mmol) and 4-nitrobenzoyl chloride (8.63 g, 46.5 mmol). After a period of 10 minutes, the reaction mixture was warmed to ambient temperature for an additional 1 hr. The reaction was diluted with EtOAc and washed with a saturated solution of $NaHCO_3$, brine, dried over Na$_2$SO$_4$, filtered through a fritted funnel and concentrated in vacuo. The crude residue was purified on silica gel and eluted with a combination of EtOAc/hexanes (1-30% EtOAc/hexanes linear gradient) which furnished the title compound.

Step H: [(3R,4R,5R,6R)-4-[(Benzyloxy)methyl]-6-{(1R)-1-[3,5-bis(trifluoromethyl)phenyl]-ethoxy}-5-(4-fluorophenyl)tetrahydro-2H-pyran-3-yl]methyl 4-nitrobenzoate The intermediate from example 1 step G (10.95 g, 17.0 mmol) was combined with (1R)-1-[3,5-bis(trifluoromethyl)phenyl]ethanol (4.39 g, 17.0 mmol) and dissolved in 170 mL DCM. The vessel was cooled to −25° C. followed by the addition boron trifluoride etherate (0.48 g, 3.4 mmol). The reaction vessel was maintained at −25° C. for 1 hr. The reaction was quenched by the addition of a saturated solution of NaHCO$_3$ and the mixture was allowed to warm to ambient temperature. The aqueous mixture was extracted several times with EtOAc and washed with brine, dried over Na$_2$SO$_4$, filtered through a fritted funnel and concentrated in vacuo. The crude residue was purified on silica gel and eluted toluene. The first component collected off the column was the unwanted diastereomer. The second component collected was the desired diastereomer and was determined to be 85% pure as determined by $^1$HNMR. The product was recrystallized from cold methanol to provide the pure title compound. $^1$H-NMR (CDCl$_3$): δ 1.41 (d, 3H, J=6.5 Hz), 1.76-1.84 (m, 1H), 2.50-2.62 (m, 1H), 3.02 (dd, 1H, J=9.0, 12.0 Hz), 3.07 (dd, 1H, J=3.0, 9.5 Hz), 3.41 (dd, 1H, J=2.5, 10.0 Hz), 3.54 (dd, 1H, J=11.5, 11.5 Hz), 4.26-4.36 (m, 5H), 4.56 (dd, 1H, J=3.5, 11.0 Hz), 4.99 (q, 1H, J=6.5 Hz), 6.92-7.06 (m, 4H), 7.20-7.36 (m, 7H), 7.71 (s, 1H), 8.19 (d, 2H, J=9.0 Hz), 8.31 (d, 2H, J=9.0 Hz) ppm.

Step I: [(3S,4R,5R,6R)-4-[(Benzyloxy)methyl]-6-{(1R)-1-[3,5-bis(trifluoromethyl)-phenyl]ethoxy}-5-(4-fluorophenyl)tetrahydro-2H-pyran-3-yl]methanol The intermediate from example 1 step H (4.57 g, 6.22 mmol) was dissolved in a 1:1 mixture of methanol/ethanol (60 mL) followed by the addition of 5 N NaOH (12.0 mL). The vessel was heated to 45° C. for 1 hr. The reaction mixture was cooled to ambient temperature and diluted with 400 mL EtOAc. The EtOAc solution was washed twice with 2 N NaOH, dried over Na$_2$SO$_4$, filtered through a fritted funnel and concentrated in vacuo. The crude residue was purified on silica gel and eluted a combination of EtOAc/hexanes (1-30% EtOAc/hexanes linear gradient). This provided the title compound. $^1$H-NMR (CDCl$_3$): δ 1.38 (d, 3H, J=6.5 Hz), 1.90-2.22 (m, 2H), 2.34-2.42 (m, 1H), 2.72 (dd, 1H, J=8.5, 10.5 Hz), 3.12-3.18 (m, 1H), 3.24-3.31 (m, 1H), 3.46-3.56 (m, 2H), 3.55-3.62 (m, 1H), 3.65-3.74 (m, 1H), 4.09 (dd, 1H, J=4.0, 11.5 Hz), 4.21 (d, 1H, J=8.5 Hz), 4.31 (s, 21H), 4.96 (q, 1H, J=6.5 Hz), 6.90-7.02 (m, 4H), 7.14-7.22 (m, 4H), 7.25-7.34 (m, 3H), 7.69 (s, 1H) ppm.

Step J: [(3S,4R,5R,6R)-6-{(1R)-1-[3,5-bis(trifluoromethyl)phenyl]ethoxy}-5-(4-fluorophenyl(tetrahydro-2H-pyran-3,4-diyl]dimethanol The intermediate from example 1 step I (3.05 g, 5.20 mmol) was combined with 1.50 g of 20% palladium hydroxide and suspended in 40 mL methanol. The flask was fitted with a 3-way stopcock and a hydrogen-filled balloon. The vessel was evacuated and purged with hydrogen five times. The mixture was maintained under 1 atm of hydrogen for 2 hr. The reaction was filtered through a pad of celite and rinsed copiously with methanol. The volatiles were removed in vacuo and the crude residue was purified on silica gel and eluted a combination of EtOAc/hexanes (1-60% EtOAc/hexanes linear gradient). This provided the title compound. $^1$H-NMR (CD$_3$OD): δ 1.35 (d, 3H, J=6.5 Hz), 1.72-1.79 (m, 1H), 1.98-2.08 (m, 1H), 2.82 (dd, 1H, J=8.5, 12.0 Hz), 3.09 (dd, 1H, J=3.5, 11.5 Hz), 3.49-3.58 (m, 3H), 3.72 (dd, 1H, J=4.0, 11.5 Hz), 4.17 (dd, 1H, J=4.0, 11.0 Hz), 4.37 (d, 1H, J=9.0 Hz), 5.04 (q, 1H, J=6.5 Hz), 6.95 (dd, 2H, J=9.0, 9.0 Hz), 7.13 (dd, 2H, J=5.5, 9.0 Hz), 7.35 (s, 2H), 7.74 (s, 1H) ppm.

Step K: (3aS,6R,7R,7aR)-2-Benzyl-6-{(1R)-1-[3,5-bis(trifluoromethyl)phenyl]ethoxy}-7-(4-fluorophenyl)octahydropyrano[3,4-c]pyrrole The intermediate from example 1 step J (1.82 g, 3.67 mmol) was combined with DMAP (0.11 g, 0.92 mmol) and dissolved in 35 mL DCM. The reaction vessel was cooled 0° C. followed by the sequential addition of triethylamine (1.49 g, 14.68 mmol) and methanesulfonyl chloride (1.05 g, 9.18 mmol). After 10 minutes, the reaction vessel was warmed to ambient temperature where it remained for 1 hr. The reaction was quenched by the addition of a saturated solution of NaHCO$_3$. The aqueous mixture was extracted several times with DCM. The combined organic extracts were washed with 1 M HCl brine, dried over Na$_2$SO$_4$, filtered through a fritted funnel and concentrated in vacuo. The crude bis-mesylate was dissolved in 20 mL n-butanol followed by the addition of benzylamine (1.57 g, 14.68 mmol). The reaction vessel was heated to 95° C. for 45 minutes. The volatiles were removed in vacuo and the crude residue was purified on silica gel and eluted with a combination of EtOAc/hexanes (35-95% EtOAc/hexanes linear gradient) which furnished the title compound. $^1$H-NMR (CD$_3$OD): δ 1.36 (d, 3H, J=6.5 Hz), 2.04-2.18 (m, 2H), 2.39 (dd, 1H, J=10.0, 10.0 Hz), 2.51 (dd, 1H, J=10.0, 10.0 Hz), 2.56 (dd, 1H, J=6.5, 9.5 Hz), 2.62 (dd, 1H, J=8.0, 11.0 Hz), 2.91 (dd, 11H, J=7.0, 10.0 Hz), 3.53 (dd, 1H, J=10.5, 10.5 Hz), 3.74 (s, 2H), 4.17 (dd, 1H, J=4.0, 11.0 Hz), 4.34 (d, 1H, J=8.0 Hz), 5.06 (q, 1H, J=6.5 Hz), 6.94 (dd, 2H, J=9.0, 9.0 Hz), 7.11 (dd, 2H, J=5.5, 9.0 Hz), 7.20-7.30 (m, 5H), 7.37 (s, 2H), 7.75 (s, 1H) ppm. MS: (MH)$^+$568.

EXAMPLE 2

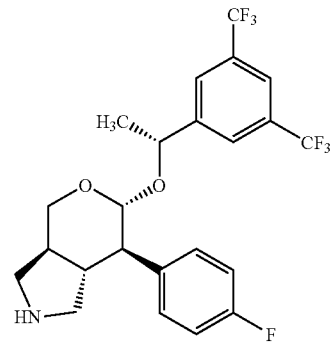

(3aS,6R,7R,7aR)-6-{(1R)-1-[3,5-Bis(trifluoromethyl)phenyl]ethoxy}-7-(4-fluorophenyl)octahydropyrano[3,4-c]pyrrole (3aS,6R,7R,7aR)-2-Benzyl-6-{(1R)-1-[3,5-bis(trifluoromethyl)phenyl]ethoxy}-7-(4-fluorophenyl)octahydropyrano[3,4-c]pyrrole (example 1: 1.60 g, 2.82 mmol) was combined 0.75 g 20% Pd(OH)$_2$ and suspended in 30 mL ethanol in a Parr apparatus. The reaction vessel was shaken vigorously under 45 psi hydrogen for 4 hr. The reaction mixture was filtered through a pad of celite and rinsed copiously with methanol. The volatiles were removed in vacuo and the crude residue was purified on silica gel and eluted with a combination of methanol/DCM (1-10% methanol/DCM linear gradient) which furnished the title compound. $^1$H-NMR (CD$_3$OD): δ 1.38 (d, 3H, J=7.0 Hz), 1.90-2.10 (m, 2H), 2.47 (dd, 1H, J=10.5, 10.5 Hz), 2.56 (dd, 1H, J=10.5, 10.5 Hz), 2.65 (dd, 1H, J=8.0, 11.0 Hz), 2.75 (dd, 1H, J=6.5, 10.5 Hz), 3.11 (dd, 1H, J=6.5, 10.0 Hz), 3.56 (dd, 1H, J=10.5, 10.5 Hz), 4.24 (dd, 1H, J=4.0, 11.0 Hz), 4.37 (d, 1H, J=8.0 Hz), 5.07 (q, 1H, J=6.5 Hz), 6.96 (dd, 2H, J=9.0, 9.0 Hz), 7.16 (dd, 2H, J=5.5, 9.0 Hz), 7.20-7.30 (m, 5H), 7.38 (s, 2H), 7.75 (s, 1H) ppm. MS: (MH)$^+$478.

EXAMPLE 3

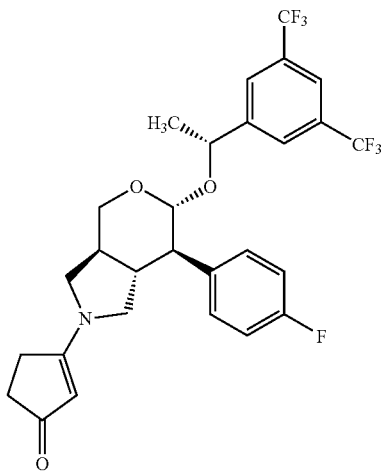

3-[(3aS,6R,7R,7aR)-6-{(1R)-1-[3,5-Bis(trifluoromethyl)phenyl]ethoxy}-7-(4-fluorophenyl)hexahydropyrano[3,4-c]pyrrol-2(3H)-yl]cyclopent-2-en-1-one (3aS,6R,7R,7aR)-6-{(1R)-1-[3,5-Bis(trifluoromethyl)phenyl]ethoxy}-7-(4-fluorophenyl)octahydropyrano[3,4-c]pyrrole (example 2: 646 mg, 1.35 mmol) was combined with 1,3-cyclopentanedione (200 mg, 2.03 mmol) and PTSA (26 mg, 0.135 mmol). Toluene (15 mL) was added to the reagents and the vessel was heated to 95° C. for 1 hr. The reaction was diluted with EtOAc and washed twice with 2N NaOH. The aqueous layer was extracted with EtOAc. The combined organic extracts were washed with brine, dried over Na$_2$SO$_4$, filtered through a fritted funnel and concentrated in vacuo. The crude residue was purified on silica gel and eluted with a 1 to 5% linear gradient of (10% NH$_4$OH-methanol)/DCM which furnished the title compound. $^1$H-NMR (CD$_3$OD): δ 1.38 (d, 3H, J=7.0 Hz), 2.20-2.44 (m, 4H), 2.55-2.84 (m, 3H), 2.80-3.24 (m, 2H), 3.34-3.80 (m, 3H), 4.24-4.34 (m, 1H), 4.42 (dd, 1H, J=2.5, 8.0 Hz), 4.78-4.92 (m, 1H), 5.09 (q, 1H, J=7.0 Hz), 6.96-7.02 (m, 2H), 7.20 (dd, 2H, J=6.05, 8.5 Hz), 7.39 (s, 2H), 7.76 (s, 1H) ppm. MS: (MH)$^+$558.

EXAMPLE 4

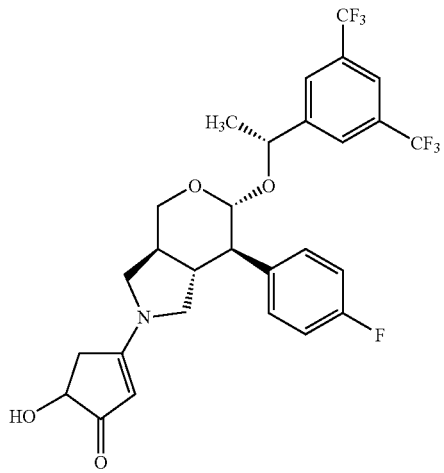

3-[(3aS,6R,7R,7aR)-6-{(1R)-1-[3,5-Bis(trifluoromethyl)phenyl]ethoxy}-7-(4-fluorophenyl)hexahydropyrano[3,4-c]pyrrol-2(3H)-yl]-5-hydroxycyclopent-2-en-1-one To a solution of 20 mg (0.0359 mmol) of 3-[(3aS,6R,7R,7aR)-6-{(1R)-1-[3,5-bis(trifluoromethyl)phenyl]ethoxy}-7-(4-fluorophenyl)hexahydropyrano[3,4-c]pyrrol-2(3H)-yl] cyclopent-2-en-1-one (example 3) and 19 mg (0.0430 mmol) MoOPH in 1.0 mL dry THF under nitrogen atmosphere at −78° C. was added 0.045 mL (0.15 mmol) of 2.0 M solution of LDA. The resulting mixture was stirred at −78° C. for 1 hr then quenched by the addition of sat. aq. Na$_2$S$_2$O$_3$. The mixture was extracted with EtOAc. The combined organic extracts were washed with brine, dried over Na$_2$SO$_4$ and filtered through a fritted funnel. The residue was purified by prep TLC eluting with 95/5 DCM/(10% NH$_4$OH/methanol) to afford the title compound as a mixture of diastereomers. $^1$H-NMR (CD$_3$OD): δ: 1.38 (d, 3H, J=6.5 Hz), 2.15-2.50 (m, 3H), 2.60-2.82 (m, 1H), 2.90-3.22 (m, 4H), 3.40-3.86 (m, 2H), 4.14-4.24 (m, 1H), 4.25-4.32 (m, 1H), 4.38-4.44 (m, 1H), 4.73-4.85 (m, 1H), 4.09 (q, 1H, J=6.5 Hz), 6.60-7.12 (m, 2H), 7.16-7.22 (m, 2H), 7.38 (s, 2H), 7.76 (s, 1H) ppm. MS: (MH)⁺574.

EXAMPLE 5

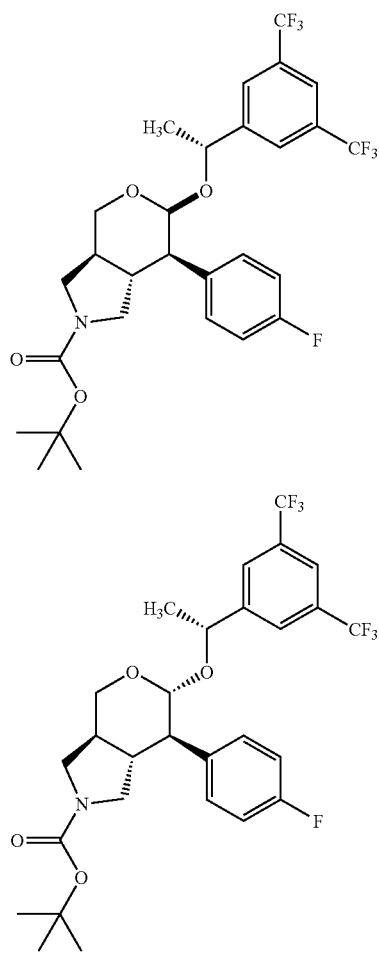

(A) tert-Butyl (3aS,6S,7R,7aR)-6-{(1R)-1-[3,5-bis(trifluoromethyl)phenyl]ethoxy}-7-(4-fluorophenyl)hexahydropyrano[3,4-c]pyrrole-2(3H)-carboxylate and (B) tert-butyl (3aS,6R,7R,7aR)-6-{(1R)-1-[3,5-bis(trifluoromethyl)phenyl]ethoxy}-7-(4-fluorophenyl)hexahydropyrano[3,4-c]pyrrole-2(3H)-carboxylate The title compound from Example 1, (3aS,6R,7R,7aR)-2-benzyl-6-{(1R)-1-[3,5-bis(trifluoromethyl)phenyl]ethoxy}-7-(4-fluorophenyl)octahydropyrano[3,4-c]pyrrole (70 mg, 0.1234 mmol), was combined with Pd(OH)₂ (50 mg), and di-tert-butyl carbonate (40 mg, 0.1851 mmol). The mixture was suspended in 5 mL methanol. The flask was fitted with a hydrogen-filled balloon attached to a 3-way stopcock. After several evacuation-hydrogen fill cycles, the reaction mixture was stirred under 1 atmosphere of hydrogen for four hr. The reaction mixture was filtered through celite, rinsed with methanol, and concentrated in vacuo. The crude residue was purified on two 1000 micron prepatory silica gel plates (eluted with 10% EtOAc/hexanes). This provide the first component (5A) eluted from the column and the second component eluted from the column (5B). Example 5A: ¹H-NMR (CDCl₃): δ 1.40-1.52 (m, 12H), 2.00-2.20 (m, 1H), 2.82-2.90 (m, 1H), 3.04-3.14 (m, 1H), 3.46-3.74 (m, 2H), 3.80-4.02 (m, 2H), 4.50-4.58 (m, 1H), 4.88-4.97 (m, 1H), 6.80-7.08 (m, 2H), 7.16-7.32 (m, 4H), 7.67 (s, 1H) ppm. MS: (M-t-butyl) 521. Example 5B: ¹H-NMR (CDCl₃): δ 1.38-1.48 (m, 12H), 1.90-2.24 (m, 2H), 2.66-2.77 (m, 1H), 2.80-2.95 (m, 2H), 3.21-3.42 (m, 1H), 3.44-3.54 (m, 1H), 3.55-3.70 (m, 1H), 4.18-4.32 (m, 2H), 5.03 (q, 1H, J=6.5 Hz), 6.94-7.12 (m, 4H), 7.20-7.26 (m, 2H), 7.72 (s, 1H) ppm.

EXAMPLE 6

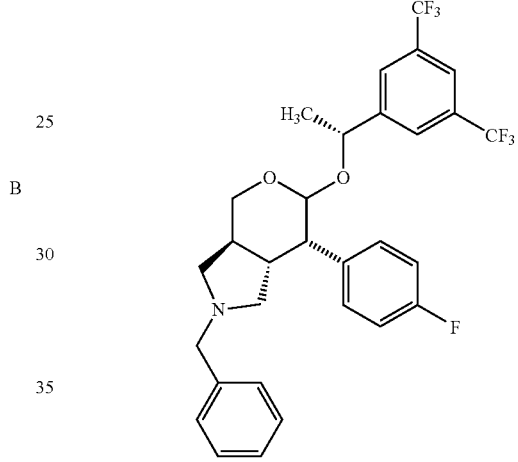

(3aS,7S,7aR)-2-Benzyl-6-{(1R)-1-[3,5-bis(trifluoromethyl)phenyl]ethoxy}-7-(4-fluorophenyl)octahydropyrano[3,4-c]pyrrole The minor diastereomers from Example 1 step C were treated under the general procedures described for example 1 for steps D-K. This furnished two diastereomeric products. MS: (MH)⁺568.

EXAMPLE 7

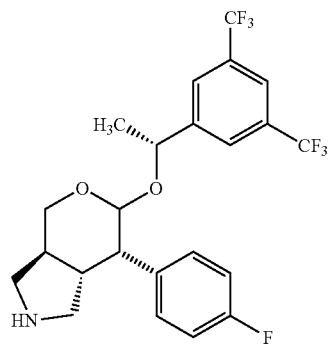

(3aS,7S,7aR)-6-{(1R)-1-[3,5-Bis(trifluoromethyl)phenyl]ethoxy}-7-(4-fluorophenyl)octahydropyrano[3,4-c]pyrrole (3aS,7S,7aR)-2-Benzyl-6-{(1R)-1-[3,5-bis(trifluoromethyl)phenyl]ethoxy}-7-(4-fluorophenyl)octahydropyrano[3,4-c]pyrrole (Example 6) was treated under the general procedures described for Example 2. This furnished the title compound. MS: (MH)$^+$478.

EXAMPLE 8

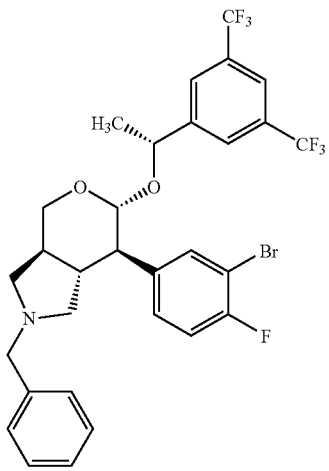

(3aS,6R,7R,7aR)-2-Benzyl-6-{(1R)-1-[3,5-bis(trifluoromethyl)phenyl]ethoxy}-7-(3-bromo-4-fluorophenyl)octahydropyrano[3,4-c]pyrrole According to the general procedures described for Example 1, 3-bromo-4-fluorophenylacetic acid was converted to title compound. $^1$H-NMR (CD$_3$OD): δ 1.39 (d, 3H, J=6.5 Hz), 2.00-2.14 (m, 2H), 2.32-2.42 (m, 1H), 2.46-2.52 (m, 1H), 2.53-2.58 (m, 1H), 2.59-2.64 (m, 1H), 2.86-2.92 (m, 1H), 3.50-3.57 (m, 1H), 3.70-3.77 (m, 1H), 4.15 (dd, 1H, J=3.5, 11.5 Hz), 4.38 (d, 1H, J=8.0 Hz), 5.04 (q, 1H, J=6.5 Hz), 7.03 (dd, 1H, J=8.5, 8.5 Hz), 7.08-7.14 (m, 1H), 7.18-7.24 (m, 1H), 7.25-7.30 (m, 4H), 7.36 (dd, 1H, J=2.0, 6.5 Hz), 7.38 (s, 2H), 7.75 (s, 1H) ppm. MS: (MH)$^+$648.

EXAMPLE 9

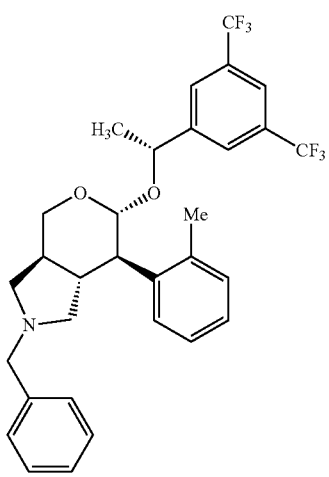

(3aS,7R,7aR)-2-Benzyl-6-{(1R)-1-[3,5-Bis(trifluoromethyl)phenyl]ethoxy}-7-(2-methylphenyl)octahydropyrano[3,4-c]pyrrole Step A: 1-[(2-methylphenyl)acetyl]piperidine The title compound was prepared from 2-methylphenylacetic acid according to the procedure for example 1, step B. $^1$H-NMR (CDCl$_3$): δ 1.42-1.62 (m, 6H), 2.28 (s, 3H), 3.42 (t, 2H), 3.61 (t, 2H), 3.67 (s, 2H), 6.84-6.91 (m, 2H), 7.09-7.16 (m, 4H) ppm. MS: (MH)$^+$218.

Step B: Dimethyl[(syn-racemic)-1-[(benzyloxy)methyl]-2-(2-methylphenyl)-3-oxo-3-piperidin-1-ylpropyl]malonate 1-[(2-methylphenyl)acetyl]piperidine (the intermediate step A, 30 g, 138 mmol) was dissolved in 500 mL THF at 0° C. was added 166 mL (166 mmol) of a 1 M solution of LHMDS. The mixture was maintained at this temperature for 1 hr and was cooled to −78° C. A solution of the intermediate from example 1 step A (37 g, 140 mmol) in ~100 mL THF was added slowly. The reaction mixture was maintained at −78° C. for 1.2 hr. The reaction was quenched with saturated aqueous solution of ammonium chloride and warmed to ambient temperature. The aqueous mixture was extracted several times with EtOAc (2×). The combined organic extracts were washed with brine, dried over Na$_2$SO$_4$, and filtered through a fritted funnel. The volatiles were removed in vacuo and the crude residue was purified on silica gel eluting with a mixture of EtOAc/hexanes (85/15) to afford the 44 g of the title compound as a mixture of syn and anti isomers.

Step C: 2-[(Syn-racemic)-1-[(Benzyloxy)methyl]-2-(2-methylphenyl)-3-oxo-3-piperidin-1-ylpropyl]propane-1,3-diol The intermediate from step B (2.0 g, 4.15 mmol) was treated according to the conditions used for example 1 step D. The crude residue was purified on silica gel (eluted with EtOAc/DCM: 1 to 75% gradient elution). This furnished the first component eluted from the column (A) and the second component (B) eluted from the column.

Step D: (3R,4R,5S and 3S,4S,5R)-4-[(Benzyloxy)methyl]-5-(hydroxymethyl)-3-(2-methylphenyl)tetrahydro-2H-pyran-2-one The intermediate component B from example 9 step C (347 mg, 0.82 mmol) was combined with PTSA (233 mg, 1.22 mol), dissolved in 15 mL toluene and heated to 80° C. in a sealed tube for 4 h. The mixture was concentrated in vacuo and the crude residue was purified on silica gel (gradient elution of 1 to 50% EtOAc/DCM). This furnished the title compound. $^1$H-NMR (CD$_3$OD): δ 2.10-2.18 (m, 1H), 2.28 (s, 3H), 2.35-2.40 (m, 1H), 3.17 (dd, 1H, J=3.5, 9.5 Hz), 3.45 (dd, 1H, J=4.0, 6.5 Hz), 3.60-3.68 (m, 2H), 4.26 (d, 1H, J=11.5 Hz), 4.38-4.44 (m, 2H), 4.48-4.58 (m, 2H), 7.10-7.20 (m, 4H), 7.22-7.38 (m, 5H) ppm. MS: (MH)$^+$341.

Step E: (3R,4R,5R and 3S,4S,5S)-4-[(Benzyloxy) methyl]-3-(2-methylphenyl)-5-{[(4-nitrobenzoyl) oxy]methyl}tetrahydro-2H-pyran-2-yl 4-nitrobenzoate The intermediate from example 9 step D was treated according to the conditions used for example 1 step F. The crude material was then treated according to the procedure described in example 1 step G. This furnished the title compound.

Step F: [(3R,4R,5R,6R)-4-[(Benzyloxy)methyl]-6-{(1R)-1-[3,5-bis(trifluoromethyl)phenyl]ethoxy}-5-(2-methylphenyl)tetrahydro-2H-pyran-3-yl]methyl 4-nitrobenzoate The intermediate from example 9 step E was treated according to the conditions used for example 1 step H. This furnished the title compound. $^1$H-NMR (CDCl$_3$): δ 1.40 (d, 3H, J=6.5 Hz), 1.88-1.96 (m, 1H), 2.45 (s, 3H), 2.58-2.66 (m, 1H), 3.10 (dd, 1H, J=3.5, 10.0 Hz), 3.38-3.46 (m, 2H), 3.57 (dd, 1H, J=11.5, 11.5 Hz), 4.24-4.40 (m, 4H), 4.56 (dd, 1H, J=4.0, 11.5 Hz), 4.95 (q, 1H, J=6.5 Hz), 6.83-6.88 (m, 1H), 7.03 (dd, 1H, J=7.0, 7.0 Hz), 7.12-7.36 (m, 9H), 7.68 (s, 1H), 8.17-8.36 (m, 4H) ppm.

Step G: [(3S,4R,5R)-4-[(Benzyloxy)methyl]-6-{(1R)-1-[3,5-bis(trifluoromethyl)phenyl]ethoxy}-5-(2-methylphenyl)tetrahydro-2H-pyran-3-yl]methanol The intermediate from example 9 step F was treated according to the conditions used for example 1 step I. This furnished the title compound. $^1$H-NMR (CD$_3$OD): δ 1.35 (d, 3H, J=6.5 Hz), 1.88-1.94 (m, 1H), 2.10-2.20 (m, 1H), 2.40 (s, 3H), 2.92-2.96 (m, 1H), 3.36-3.39 (m, 1H), 3.44-3.50 (m, 1H), 3.54-3.60 (m, 1H), 3.68-3.73 (m, 1H), 4.18-4.42 (m, 4H), 4.88 (q, 1H, J=6.5 Hz), 6.88-6.98 (m, 2H), 7.02-7.38 (m, 8H), 7.72 (s, 1H) ppm.

Step H: [(3S,4R,5R)-6-{(1R)-1-[3,5-Bis(trifluoromethyl)phenyl]ethoxy}-5-(2-methylphenyl)tetrahydro-2H-pyran-3,4-diyl]dimethanol The intermediate from example 9 step G was treated according to the conditions used for example 1 step J. This furnished the title compound.

Step I: (3aS,7R,7aR)-2-Benzyl-6-{(1R)-1-[3,5-bis(trifluoromethyl)phenyl]ethoxy}-7-(2-methylphenyl)octahydropyrano[3,4-c]pyrrole The intermediate from example 9 step H was treated according to the conditions used for example 1 step K. This furnished the title compound. MS: (MH)$^+$564.

EXAMPLE 10

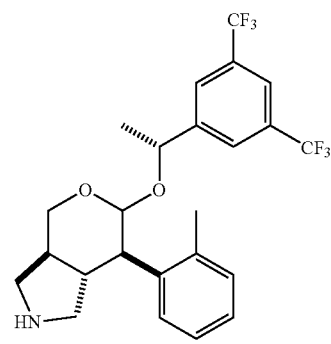

(3aS,7R,7aR)-6-{(1R)-1-[3,5-Bis(trifluoromethyl)phenyl]ethoxy}-7-(2-methylphenyl)octahydropyrano[3,4-c]pyrrole (3aS,7R,7aR)-2-Benzyl-6-{(1R)-1-[3,5-bis(trifluoromethyl)phenyl]ethoxy}-7-(2-methylphenyl)octahydropyrano[3,4-c]pyrrole (example 9) was treated according to the conditions used for example 2. This furnished the title compound. MS: (MH)$^+$474.

EXAMPLE 11

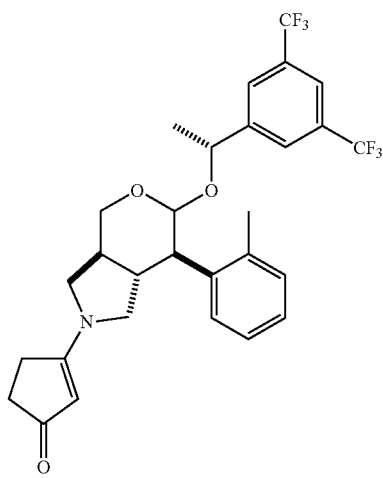

3-[(3aS,7R,7aR)-6-{(1R)-1-[3,5-Bis(trifluoromethyl)phenyl]ethoxy}-7-(2-methylphenyl)hexahydropyrano[3,4-c]pyrrol-2(3H)-yl]cyclopent-2-en-1-one (3aS,7R,7aR)-6-{(1R)-1-[3,5-Bis(trifluoromethyl)phenyl]ethoxy}-7-(2-methylphenyl)octahydropyrano[3,4-c]pyrrole was prepared from Example 10 and cyclopentane-1,3-dione according to the procedures used for example 3. MS: (MH)$^+$554.

EXAMPLE 12

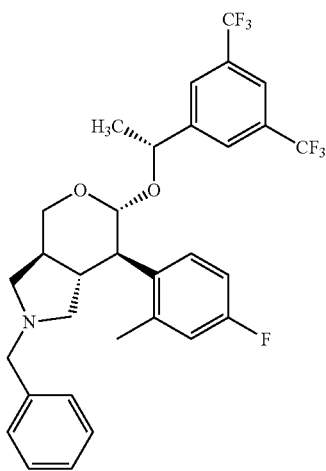

(3aS,6R,7R,7aR)-2-benzyl-6-{(1R)-1-[3,5-bis(trifluoromethyl)phenyl]ethoxy}-7-(4-fluoro-2-methylphenyl)octahydropyrano[3,4-c]pyrrole

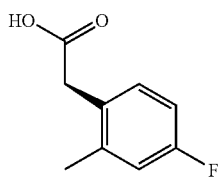

Step A: 4-Fluoro-2-methylphenylacetic acid

To a 2 L flask containing 2-dicyclohexylphosphino-2'-(N,N-dimethylamino)biphenyl.(3.76 g) and Pd(OAc)$_2$ (1.02 g) were added 396 mL of 1 N LHMDS in hexanes, then 400 mL of toluene under N$_2$. The solution was cooled to −10° C. and tButyl acetate (49 mL was added. The solution was stirred at −10° C. for 10 min and was added 2-bromo-5-fluoro toluene. The mixture was heated at 80° C. for 15 min and was washed with NH$_4$Cl and NaCl, dried with Na$_2$SO$_4$, filtered and concentrated. The crude was purified by flash chromatorghy with EtOAc/hexanes=1:30 to give tert-butyl (4-fluoro-2-methylphenyl)acetate (21.85 g).

The pure ester was dissolved in 60 ml of CH$_2$Cl$_2$ was added 6 drops of anisole and 60 ml of CF$_3$CO$_2$H and the solution was atirred at rt for 16 hr. Upon removal of volatiles, the residue was dried three times by dissolving in toluene to afford 20.02 g of the title compound. $^1$H-NMR (CDCl$_3$): δ 2.35 (s, 3H), 3.67 (s, 2H), 6.92-6.95 (m, 2H), 7.19 (d of d, 1H, J=8.2, 5.7 Hz) ppm.

Step B: 1-[(4-Fluoro-2-methylphenyl)acetyl]piperidine

The title compound was prepared from 4-fluoro-2-methylphenylacetic acid as for example 1, step B. $^1$H-NMR (CDCl$_3$): δ 1.28-1.67 (m, 6H), 2.28 (s, 3H), 3.39 (t, 2H), 3.62 (t, 2H), 3.64 (s, 2H), 6.84-6.91 (m, 2H), 7.09 (d of d, 1H, J=8.4, 5.9 Hz) ppm.

Step C: Dimethyl[1-[(benzyloxy)methyl]-2-(4-fluoro-2-methyphenyl)-3-oxo-3-piperidin-1-ylpropyl]malonate 1-[(4-Fluoro-2-methylphenyl)acetyl]piperidine (the intermediate step B, 11.88 g, 50.5 mmol) was dissolved in 290 mL THF at 0° C. was added 60.6 mL (60.6 mmol) of a 1 M solution of LHMDS. The mixture was maintained at this temperature for 1 hr and was cooled to −78° C. A solution of the intermediate from example 1, step A (16.03 g, 60.6 mmol) in 50 mL THF was added slowly. The reaction mixture was maintained at −78° C. for 1.2 hr. The reaction was quenched with saturated aqueous solution of ammonium chloride and warmed to ambient temperature. The aqueous mixture was extracted several times with EtOAc (2×). The combined organic extracts were washed with brine, dried over Na$_2$SO$_4$, and filtered through a fritted funnel. The volatiles were removed in vacuo and the crude residue was purified on silica gel eluting with a mixture of EtOAc/hexanes (10-30% gradient elution) to afford the title compound as a mixture of syn and anti isomers. On small scale chromatography, the first component eluted off the column (A) was identified as the anti isomer and the second component (B) was the syn isomer.

Step D: 2-syn-[1-[(Benzyloxy)methyl]-2-(4-fluoro-2-methylphenyl)-3-oxo-3-piperidin-1-ylpropyl]propane-1,3-diol The intermediate from step C (23.01 g, 46.1 mmol) was dissolved in 250 mL THF and cooled to 0° C. Lithium borohydride (15.01 g, 692 mmol) was added in a single portion. After stirring 30 minutes at 0° C., the reaction was warmed to ambient temperature where it was maintained for 72 hr. The reaction was cooled to 0° C., cautiously quenched with a saturated solution of ammonium chloride and warmed to ambient temperature for 1 hr. The aqueous solution was extracted with EtOAc (2×500 mL). The combined organic fractions were washed with brine, dried over Na$_2$SO$_4$, and filtered through a fritted funnel. The volatiles were removed in vacuo and the crude residue was purified on silica gel and eluted first with a mixture of EtOAc/dichloromethane (75% gradient elution) then MeOH/dichloromethane. This provided the less polar anti isomer (A) and the syn title compound (B). MS: (MH)$^+$444.

Step E: Racemic (3R,4R,5S and 3S,4S,5R)-4-[(benzyloxy)methyl]-3-(4-fluoro-2-methylphenyl)-5-(hydroxymethyl)tetrahydro-2H-pyran-2-one The syn intermediate from example 1 step D (6.92 g, 15.6 mmol) was dissolved in 200 mL toluene/CH2Cl2 (3:1) and was added methanesulfonic acid (1.41 mL, 21.8 mmol). The reaction mixture was maintained at ambient temperature for 16 hr. The reaction was quenched with a saturated solution of NaHCO₃ and extracted with EtOAc (3×300 mL). The combined organic extracts were washed with brine, dried over Na₂SO₄, filtered through a fritted funnel and concentrated in vacuo. The crude residue was purified on silica gel with EtOAc/hexanes=50%. MS: (M+Na)⁺381.

Step F: Racemic-(2R,3R,4R,5R and 2S,3S,4S,5S)-4-[(benzyloxy)methyl]-3-(4-fluoro-2-methylphenyl)-5-{[(4-nitrobenzoyl)oxy]methyl}tetrahydro-2H-pyran-2-yl 4-nitrobenzoate The intermediate from step E (3.75, 10.5 mmol) was dissolved in 66 mL DCM and cooled to −78° C. A 1.0 M solution of DIBAL-H (26.1 mL, in toluene) was added dropwise. The reaction was maintained at −78° C. for 60 minutes and was quenched with 0.25 mL of MeOH. After it was warmed to rt, the solution was diluted with ether/EtOAc (1:1, 600 mL) and was added solid Na₂SO₄10H₂O. The suspension was stirred at rt for 1 h and was added Na₂SO₄. After 10 min, the mixture was filtered through a fritted funnel and concentrated in vacuo to afford racemic-(2S,3R,4R,5S and 2R,3S,4S,5R)-4-[(benzyloxy)methyl]-3-(4-fluoro-2-methylphenyl)-5-(hydroxymethyl)tetrahydro-2H-pyran-2-ol._MS: (M+Na)⁺383.

The lactol intermediate was dissolved in 80 mL DCM and cooled 0° C. followed by the addition of DMAP (0.017 g, 0.014 mmol), triethylamine (5.7 mL, 40.9 mmol) and 4-nitrobenzoyl chloride (4.83 g, 26.0 mmol). After a period of 10 minutes, the reaction mixture was warmed to ambient temperature for an additional 1 hr. The reaction was diluted with EtOAc and washed with a saturated solution of NaHCO₃, brine, dried over Na₂SO₄, filtered through a fritted funnel and concentrated in vacuo. The crude residue was purified on silica gel and eluted with a combination of EtOAc/hexanes (1-30% EtOAc/hexanes linear gradient) which furnished the title compound.

Step G: [(3R,4R,5R,6R)-4-[(Benzyloxy)methyl]-6-{(1R)-1-[3,5-bis(trifluoromethyl)phenyl]-ethoxy}-5-(4-fluoro-2-methylphenyl)tetrahydro-2H-pyran-3-yl]methyl 4-nitrobenzoate The intermediate from step F (6.17 g, 9.36 mmol) was combined with (1R)-1-[3,5-bis(trifluoromethyl)phenyl]ethanol (2.53 g, 9.83 mmol) and dissolved in 100 mL DCM. The vessel was cooled to −25° C. followed by the addition boron trifluoride etherate (0.23 mL, 1.87 mmol). The reaction vessel was maintained at −25° C. for 1 hr. The reaction was quenched by the addition of a saturated solution of NaHCO₃ and the mixture was allowed to warm to ambient temperature. The aqueous mixture was extracted several times with EtOAc and washed with brine, dried over Na₂SO₄, filtered through a fritted funnel and concentrated in vacuo. The crude residue was purified on silica gel and eluted with tBuOMe/hexanes=10 to 14%. The first component collected off the column was the desired diastereomer. (M+Na)⁺772

Step H: [(3S,4R,5R,6R)-4-[(Benzyloxy)methyl]-6-{(1R)-1-[3,5-bis(trifluoromethyl)-phenyl]ethoxy}-5-(4-fluoro-2-methylphenyl)tetrahydro-2H-pyran-3-yl]methanol The intermediate from step G (3.98 g, 5.31 mmol) was dissolved in 100 mL of MeOH and was added 0.1 mL of 2N NaOH. The mixture was heated to 45° C. for 1 hr. Volatiles were removed in vacuo. The crude residue was purified on silica gel and eluted a combination of EtOAc/hexanes (10-30% EtOAc/hexanes linear gradient). This provided the title compound. MS: (MH)⁺601

Step I: [(3S,4R,5R,6R)-6-{(1R)-1-[3,5-bis(Trifluoromethyl)phenyl]ethoxy}-5-(4-fluoro-2-methylphenyl)tetrahydro-2H-pyran-3,4-diyl]dimethanol The intermediate from H step I (2.87 g, 4.78 mmol) was combined with 0.50 g of 20% palladium hydroxide on carbon and suspended in 80 mL methanol. The flask was shaken under 23 PSI of hydrogen for 50 min. The reaction was filtered through a pad of celite and rinsed copiously with methanol. The volatiles were removed in vacuo provided the title compound.

Step J: (3aS,6R,7R,7aR)-2-Benzyl-6-{(1R)-1-[3,5-bis(trifluoromethyl)phenyl]ethoxy}-7-(4-fluoro-2-methylphenyl)octahydropyrano[3,4-c]pyrrole The intermediate from step I (2.44 g, 4.87 mmol) was combined with DMAP (0.15 g, 1.2 mmol) and dissolved in 38 mL DCM. The reaction vessel was cooled 0° C. followed by the sequential addition of triethylamine (2.72 mL, 19.5 mmol) and methanesulfonyl chloride (0.95 mL, 12.2 mmol). After 5 minutes, the reaction vessel was warmed to ambient temperature where it remained for 0.5 hr. The reaction was quenched by the addition of a saturated solution of NaHCO₃. The aqueous mixture was extracted several times with DCM. The combined organic extracts were washed with 1 M HCl, brine, dried over Na₂SO₄, filtered through a fritted funnel and concentrated in vacuo. The crude bis-mesylate was dissolved in 50 mL n-butanol followed by the addition of benzylamine (3.19 mL, 29.2 mmol). The reaction vessel was heated to 100° C. for 3.5 hr. The volatiles were removed in vacuo and the crude residue was purified on silica gel and eluted with a combination of EtOAc/hexanes (35-95% EtOAc/hexanes linear gradient) which furnished the title compound. MS: (MH)⁺ 582.

EXAMPLE 13

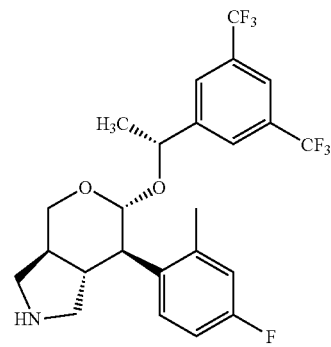

(3aS,6R,7R,7aR)-6-{(1R)-1-[3,5-bis(Trifluoromethyl)phenyl]ethoxy}-7-(4-fluoro-2-methylphenyl)octahydropyrano[3,4-c]pyrrole (3aS,6R,7R,7aR)-2-Benzyl-6-{(1R)-1-[3,5-bis(trifluoromethyl)phenyl]ethoxy}-7-(4-fluoro-2-methylphenyl)octahydropyrano[3,4-c]pyrrole (example 1: 2.51 g, 4.32 mmol) was combined 0.5 g 20% Pd(OH)$_2$/C and suspended in 100 mL ethanol in a Parr apparatus. The reaction vessel was shaken vigorously under 45 psi hydrogen for 7 hr. The reaction mixture was filtered through a pad of celite and rinsed copiously with methanol. The volatiles were removed in vacuo and the crude residue was purified on silica gel and eluted with a combination of DCM/methanol/NH4OH=90:9:1. MS: (MH)$^+$492.

EXAMPLE 14

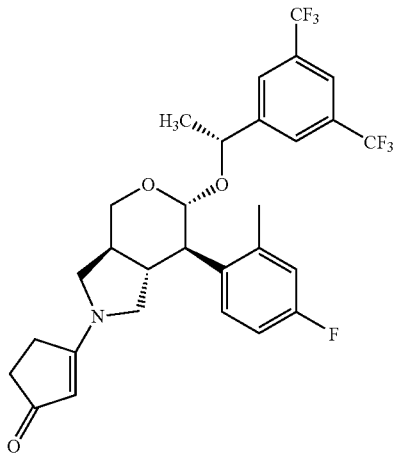

3-[(3aS,7R,7aR)-6-{(1R)-1-[3,5-bis(Trifluoromethyl)phenyl]ethoxy}-7-(4-fluoro-2-methylphenyl)hexahydropyrano[3,4-c]pyrrol-2(3H)-yl]cyclopent-2-en-1-one The title compound was prepared from (3aS,6R,7R,7aR)-6-{(1R)-1-[3,5-bis(trifluoromethyl)phenyl]ethoxy}-7-(4-fluoro-2-methylphenyl)octahydropyrano[3,4-c]pyrrole and cyclopentane-1,3-dione according to the procedures used for example 3. MS: (MH)$^+$572.

EXAMPLE 15

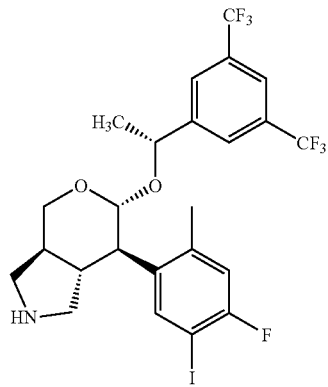

(3aS,6R,7R,7aR)-6-{(1R)-1-[3,5-bis(Trifluoromethyl)phenyl]ethoxy}-7-(4-fluoro-5-iodo-2-methylphenyl)octahydropyrano[3,4-c]pyrrole A solution of (3aS,6R,7R,7aR)-6-{(1R)-1-[3,5-bis(trifluoromethyl)phenyl]ethoxy}-7-(4-fluoro-2-methylphenyl)octahydropyrano[3,4-c]pyrrole (55.8 mg, 0.12 mmol) and NIS (53 mg, 0.23 mmol) in 2 mL trifluoroacetic acid was stirred at rt for 40 min. Volatiles were removed. The crude was purified by reverse phase HPLC to afford the title compound.

EXAMPLE 16

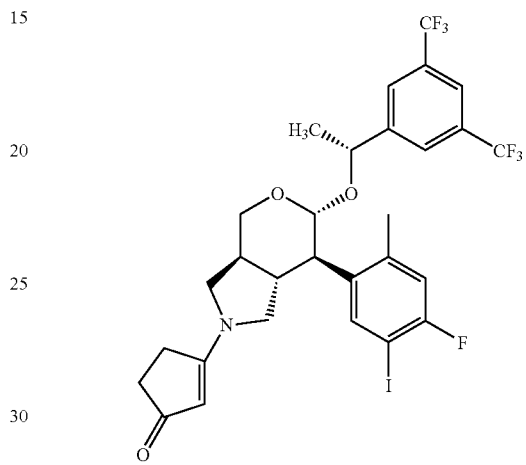

3-[(3aS,7R,7aR)-6-{(1R)-1-[3,5-bis(Trifluoromethyl)phenyl]ethoxy}-7-(4-fluoro-5-iodo-2-methylphenyl)hexahydropyrano[3,4-c]pyrrol-2(3H)-yl]cyclopent-2-en-1-one The title compound was prepared from (3aS,6R,7R,7aR)-6-{(1R)-1-[3,5-bis(trifluoromethyl)phenyl]ethoxy}-7-(4-fluoro-5-iodo-2-methylphenyl)octahydropyrano[3,4-c]pyrrole and cyclopentane-1,3-dione according to the procedures used for example 3. MS: (MH)$^+$698.

EXAMPLE 17

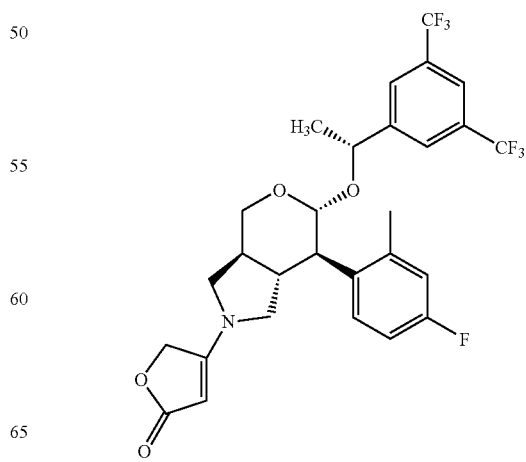

4-[(3aS,6R,7R,7aR)-6-{(1R)-1-[3,5-bis (Trifluoromethyl)phenyl]ethoxy}-7-(4-fluoro-2-methylphenyl)hexahydropyrano[3,4-c]pyrrol-2(3H)-yl]furan-2(5m)-one A solution of (3aS,6R,7R,7aR)-6-{(1R)-1-[3,5-bis(trifluoromethyl)phenyl]ethoxy}-7-(4-fluoro-2-methylphenyl)octahydropyrano[3,4-c]pyrrole (81.8 mg, 0.17 mmol) and furan-2,4(3H, 5H)-dione (50 mg, 0.50 mmol) in 4 mL of HOAc was heated in a 120° C. oil bath for 1 h. Then 2 mL of toluene was added and the mixture was heated for another 2.5 hr at 120° C. Volatiles were removed and residue was purified by reverse phase HPLC to afford the title compound. MS: (MH)+574.

EXAMPLE 18

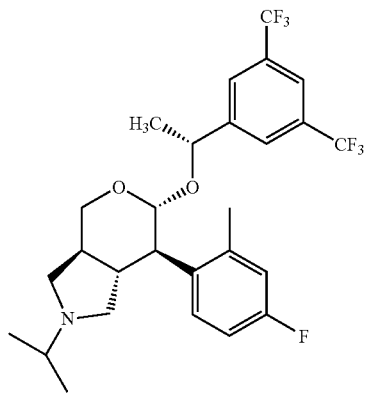

(3aS,6R,7R,7aR)-6-{(1R)-1-[3,5-bis(Trifluoromethyl)phenyl]ethoxy}-7-(4-fluoro-2-methylphenyl)-2-isopropyloctahydropyrano[3,4-c]pyrrole To a solution of (3aS,6R,7R,7aR)-6-{(1R)-1-[3,5-bis(trifluoromethyl)phenyl]ethoxy}-7-(4-fluoro-2-methylphenyl) octahydropyrano[3,4-c]pyrrole (29.6 mg, 0.06 mmol), acetone (0.044 mL, 0.60 mmol) and NaB(OAc)$_3$H (69 mg, 0.33 mmol) in DCM was added 1 drop of HOAc and was stirred at rt for 16 hr. The mixture was diluted with DCM and was washed with NaHCO$_3$. The organic phase was dried with Na$_2$SO$_4$, filtered and concentrated. The crude was purified by reverse phase HPLC to afford the title compound. MS: (MH)+ 534.

EXAMPLE 19

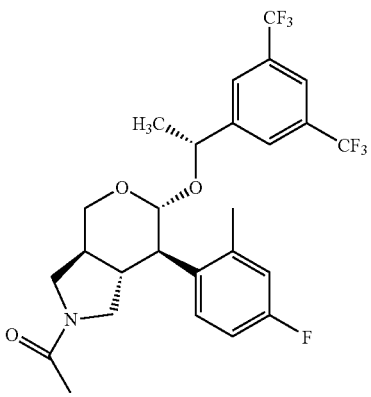

(3aS,6R,7R,7aR)-2-acetyl-6-{(1R)-1-[3,5-bis(Trifluoromethyl)phenyl]ethoxy}-7-(4-fluoro-2-methylphenyl)octahydropyrano[3,4-c]pyrrole A solution of (3aS,6R,7R,7aR)-6-{(1R)-1-[3,5-bis(trifluoromethyl)phenyl]ethoxy}-7-(4-fluoro-2-methylphenyl)octahydropyrano[3,4-c]pyrrole (29 mg, 0.059 mmol), DMAP (1 mg) and acetic anhydride (0.028 mL, 0.30 mmol) in 2 mL of pyridine was stirred at rt for 4 hr. Volatiles were removed and the crude was purified by reverse phase HPLC to afford the title compound. MS: (MH)+534.

EXAMPLE 20

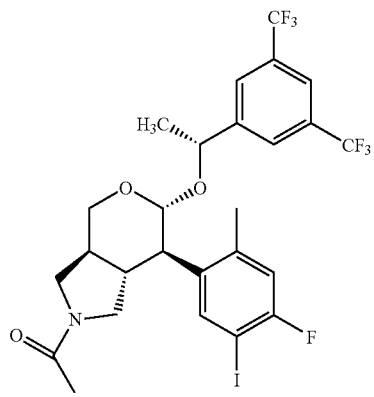

(3aS,6R,7R,7aR)-2-acetyl-6-{(1R)-1-[3,5-bis(Trifluoromethyl)phenyl]ethoxy}-7-(4-fluoro-5-iodo-2-methylphenyl)octahydropyrano[3,4-c]pyrrole The title compound was prepared from (3aS,6R,7R,7aR)-6-{(1R)-1-[3,5-bis(trifluoromethyl)phenyl]ethoxy}-7-(4-fluoro-5-iodo-2-methylphenyl)octahydropyrano[3,4-c]pyrrole and acetic anhydride according to the procedures used for example 19. MS: (MH)+660.

EXAMPLE 21

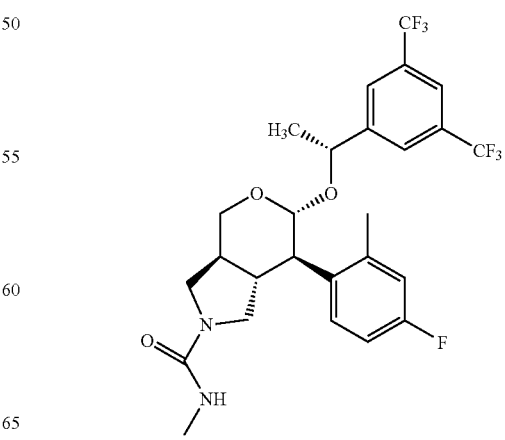

35

(3AS,6R,7R,7AR)-6-{(1R)-1-[3,5-Bis(Trifluoromethyl)phenyl]ethoxy}-7-(4-fluoro-2-methylphenyl)-N-methylhexahydropyrano[3,4-C]pyrrole-2(3H)-carboxamide A solution of (3aS,6R,7R,7aR)-6-{(1R)-1-[3,5-bis(trifluoromethyl)phenyl]ethoxy}-7-(4-fluoro-2-methylphenyl)octahydropyrano[3,4-c]pyrrole (15 mg, 0.032 mmol) in 2.5 mL of DCM was added 3 drops of methyl isocynate. The solution was stirred at rt for 1 hr. Volatiles were removed and the crude was purified by reverse phase HPLC to afford the title compound. MS: (MH)$^+$549.

EXAMPLE 22

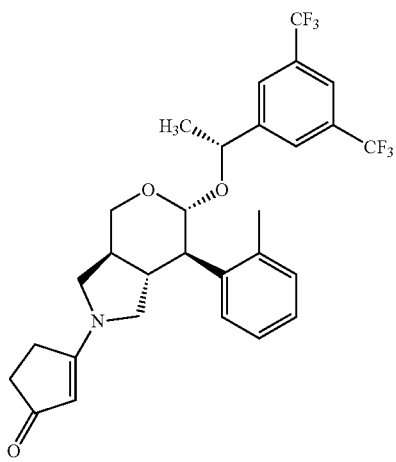

3-[(3aS,7R,7aR)-6-{(1R)-1-[3,5-Bis(Trifluoromethyl)phenyl]ethoxy}-7-(2-methylphenyl)hexahydropyrano[3,4-c]pyrrol-2(3H)-yl]cyclopent-2-en-1-one The title compound was prepared from (3aS,6R,7R,7aR)-6-{(1R)-1-[3,5-bis(trifluoromethyl)phenyl]ethoxy}-7-(2-methylphenyl)octahydropyrano[3,4-c]pyrrole and cyclopentane-1,3-dione according to the procedures used for example 3. MS: (MH)$^+$554.

EXAMPLE 23

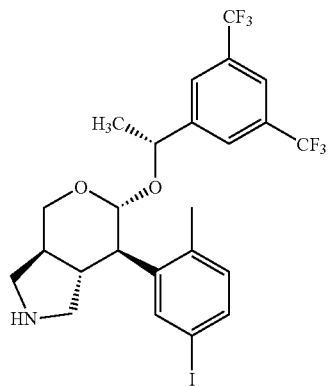

36

(3aS,6R,7R,7aR)-6-{(1R)-1-[3,5-bis(Trifluoromethyl)phenyl]ethoxy}-7-(5-iodo-2-methylphenyl)octahydropyrano[3,4-c]pyrrole The title compound was prepared from (3aS,6R,7R,7aR)-6-{(1R)-1-[3,5-bis(trifluoromethyl)phenyl]ethoxy}-7-(2-methylphenyl)octahydropyrano[3,4-c]pyrrole according to the procedures used for example 15. MS: (MH)$^+$600.

EXAMPLE 24

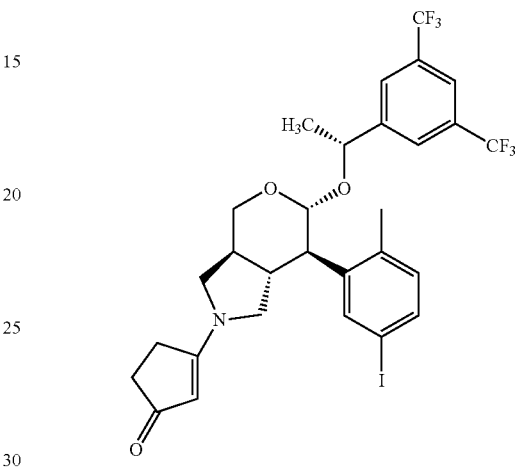

3-[(3aS,6R,7R,7aR)-6-{(1R)-1-[3,5-bis(Trifluoromethyl)phenyl]ethoxy}-7-(5-iodo-2-methylphenyl)hexahydropyrano[3,4-c]pyrrol-2(3H)-yl]cyclopent-2-en 1-one The title compound was prepared from (3aS,6R,7R,7aR)-6-{(1R)-1-[3,5-bis(trifluoromethyl)phenyl]ethoxy}-7-(5-iodo-2-methylphenyl)octahydropyrano[3,4-c]pyrrole according to the procedures used for example 3. MS: (MH)$^+$ 680.

EXAMPLE 25

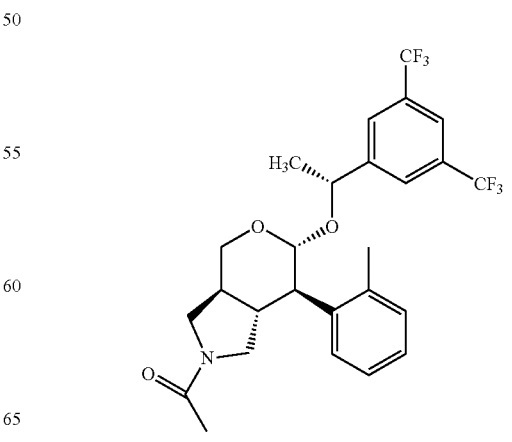

(3aS,6R,7R,7aR)-2-Acetyl-6-{(1R)-1-[3,5-bis(trifluoromethyl)phenyl]ethoxy}-7-(2-methylphenyl)octahydropyrano[3,4-c]pyrrole The title compound was prepared from (3aS,6R,7R,7aR)-6-{(1R)-1-[3,5-bis(trifluoromethyl)phenyl]ethoxy}-7-(2-methylphenyl)octahydropyrano[3,4-c]pyrrole and acetic anhydride according to the procedures used for example 19. MS: (MH)$^+$516.

EXAMPLE 26

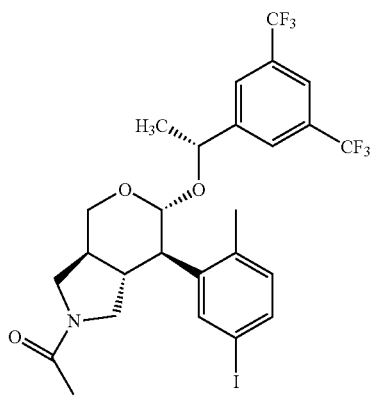

(3aS,6R,7R,7aR)-2-Acetyl-6-{(1R)-1-[3,5-bis(trifluoromethyl)phenyl]ethoxy}-7-(5-iodo-2-methylphenyl)octahydropyrano[3,4-c]pyrrole The title compound was prepared from (3aS,6R,7R,7aR)-6-{(1R)-1-[3,5-bis(trifluoromethyl)phenyl]ethoxy}-7-(5-iodo-2-methylphenyl)octahydropyrano[3,4-c]pyrrole and acetic anhydride according to the procedures used for example 19. MS: (MH)$^+$642.

EXAMPLE 27

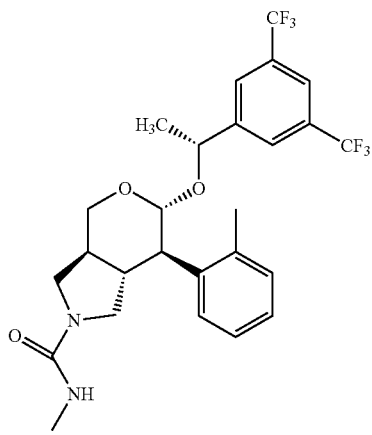

(3aS,6R,7R,7aR)-6-{(1R)-1-[3,5-bis(Trifluoromethyl)phenyl]ethoxy}-N-methyl-7-(2-methylphenyl)hexahydropyrano[3,4-c]pyrrole-2(3H)-carboxamide The title compound was prepared from (3aS,6R,7R,7aR)-6-{(1R)-1-[3,5-bis(trifluoromethyl)phenyl]ethoxy}-7-(2-methylphenyl)octahydropyrano[3,4-c]pyrrole according to the procedures used for example 21. MS: (MH)$^+$531.

Using the procedures essentially comparable to those described above or by procedures known to those skilled in the art the compounds of the following Examples were prepared.

| Ex | R$^1$ | X | MS |
|---|---|---|---|
| 28 | ![2-methyl-3-oxocyclopent-1-enyl] | 4-F | 572.5 (M + H) |
| 29 | ![5-oxo-2,5-dihydrofuran-3-yl] | 4-F | 560.3 (M + H) |

| Ex. # | R$^1$ | X |
|---|---|---|
| 30 | ![acetyl] | 4-F |

-continued

| 31 | Me | 4-F |
| 32 | 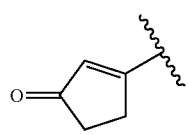 | H |
| 33 | 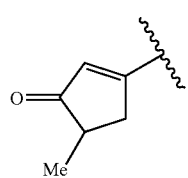 | 4-F |
| 34 | 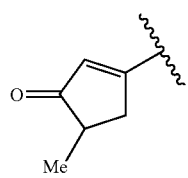 | 2-Me |
| 35 | 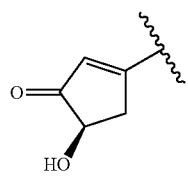 | 2-Me |
| 36 | 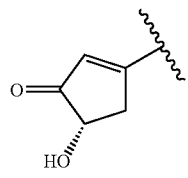 | 2-Me |
| 37 | 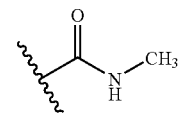 | 4-F |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

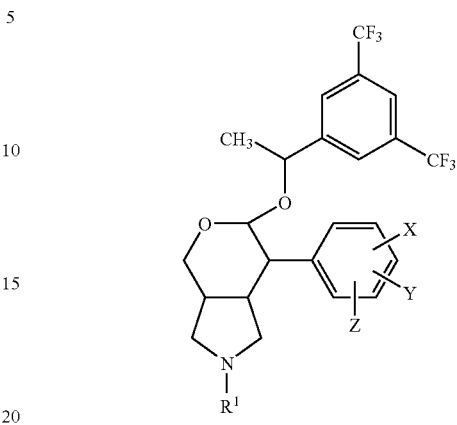

I wherein:
$R^1$ is selected from the group consisting of:
  (1) hydrogen,
  (2) $C_{1-6}$alkyl, which is unsubstituted or substituted with halogen, hydroxyl or phenyl,
  (3) cyclopentenone, which is unsubstituted or substituted with hydroxyl or methyl,
  (4) furanone, which is unsubstituted or substituted with methyl,
  (5) —(CO)—$C_{1-6}$alkyl,
  (6) —(CO)—$NH_2$,
  (7) —(CO)—$NHC_{1-6}$alkyl, and
  (8) —(CO)—$N(C_{1-6}$alkyl)($C_{1-6}$alkyl);
X, Y and Z are independently selected from the group consisting of:
  (1) hydrogen,
  (2) halo, and
  (3) methyl;
and pharmaceutically acceptable salts thereof and individual enantiomers and diastereomers thereof.

2. The compound of claim 1 of the formula Ia:

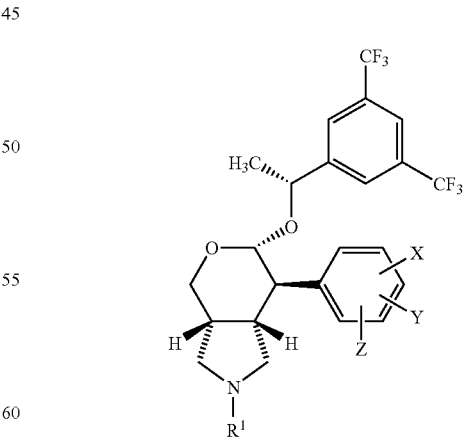

Ia and pharmaceutically acceptable salts thereof and individual enantiomers and diastereomers thereof.

3. The compound of claim 1 of the formula Ib:

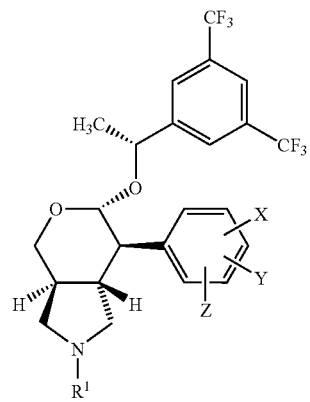

Ib and pharmaceutically acceptable salts thereof and individual enantiomers and diastereomers thereof.

4. The compound of claim 1 wherein $R^1$ is selected from the group consisting of:
   (1) hydrogen,
   (2) $C_{1-3}$alkyl, which is unsubstituted or substituted with hydroxyl or phenyl,
   (3) cyclopent-2-en-1-one, which is unsubstituted or substituted with hydroxyl or methyl,
   (4) furanone, which is unsubstituted or substituted with methyl,
   (5) —(CO)—$C_{1-3}$alkyl,

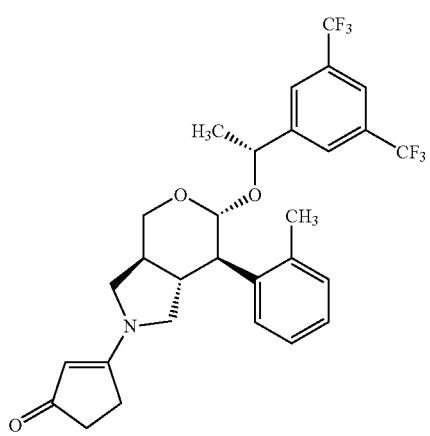

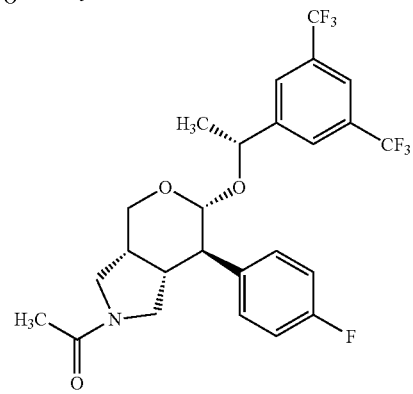

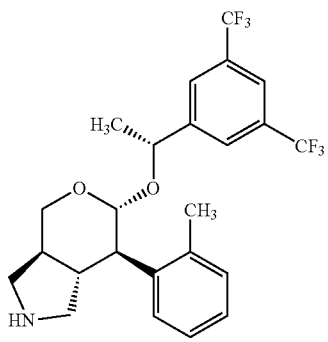

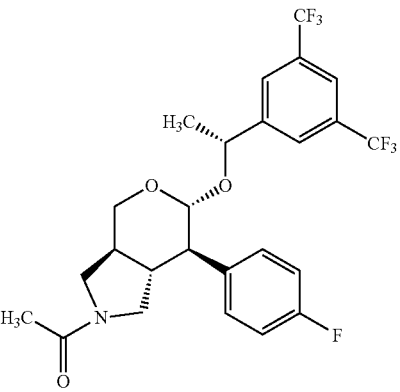

(6) —(CO)—$NH_2$,
   (7) —(CO)—$NHC_{1-3}$alkyl, and
   (8) —(CO)—$N(C_{1-3}$alkyl)($C_{1-3}$alkyl).

5. The compound of claim 1 wherein $R^1$ is selected from the group consisting of:
   (1) hydrogen,
   (2) methyl,
   (3) 2-phenylethyl,
   (4) 2-hydroxyethyl,
   (5) cyclopent-2-en-1-one,
   (6) 5-hydroxycyclopent-2-en-1-one,
   (7) 4-hydroxycyclopent-2-en-1-one,
   (8) 2-methylcyclopent-2-en-1-one,
   (9) 5-furanone,
   (10) acetyl,
   (11) acetamido,
   (12) methyl-acetamido, and
   (13) dimethyl-acetamido.

6. The compound of claim 1 wherein X is fluorine, Y is hydrogen, and Z is hydrogen.

7. The compound of claim 1 wherein X is methyl, Y is hydrogen, and Z is hydrogen.

8. A compound which is selected from the group consisting of:
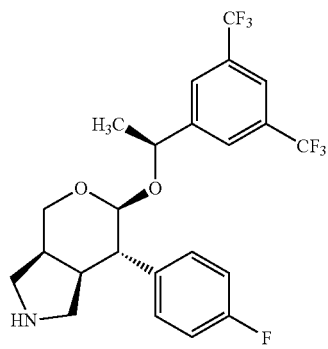
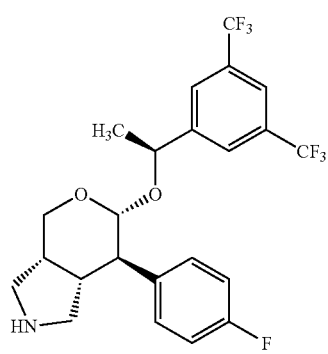
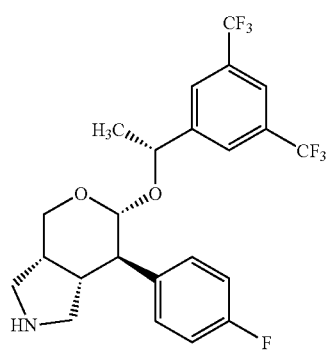
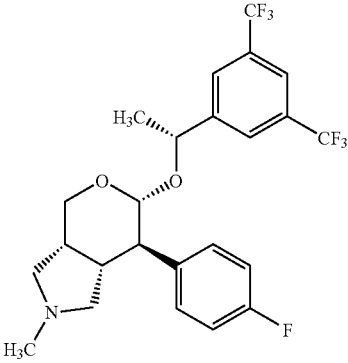
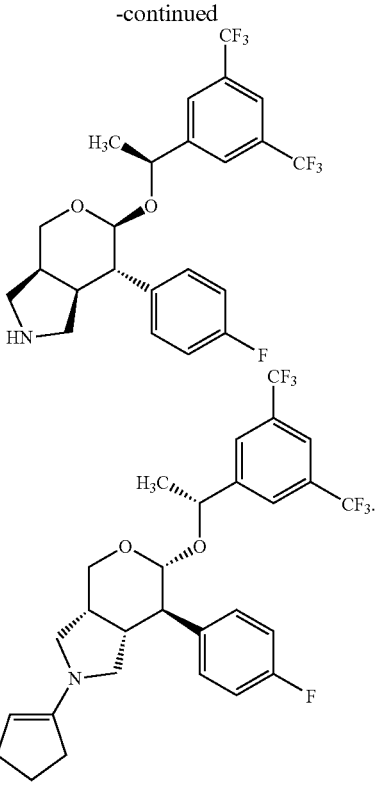
9. A compound of claim 1 selected from the group consisting of
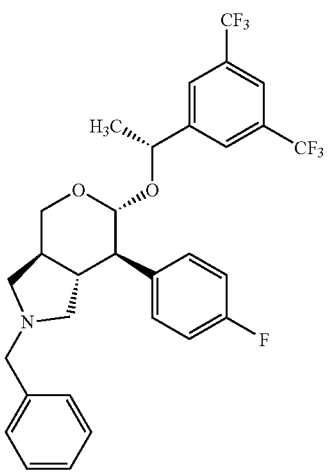
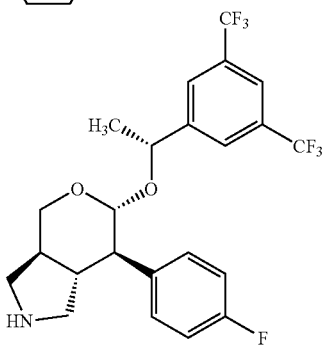

-continued
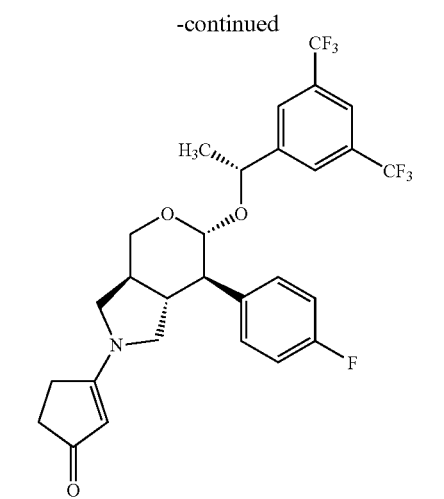
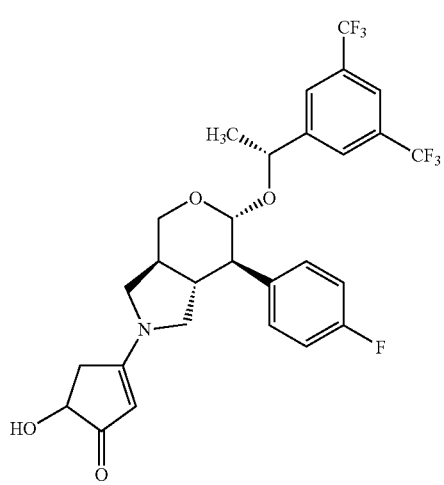
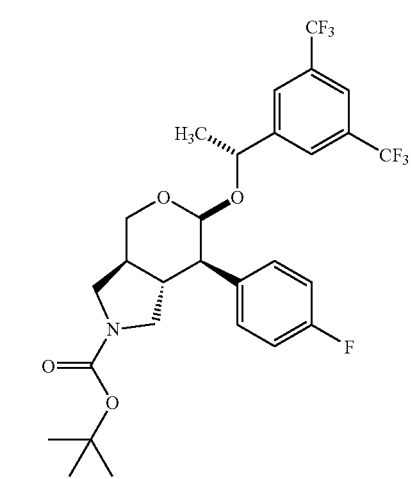
A
-continued
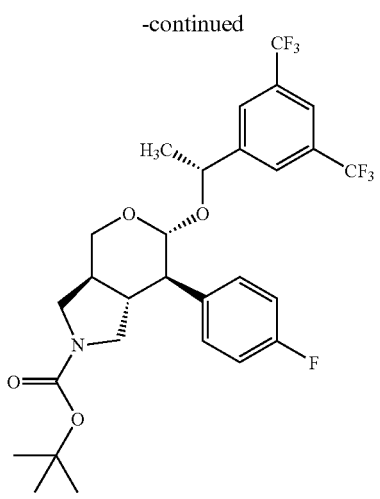
B
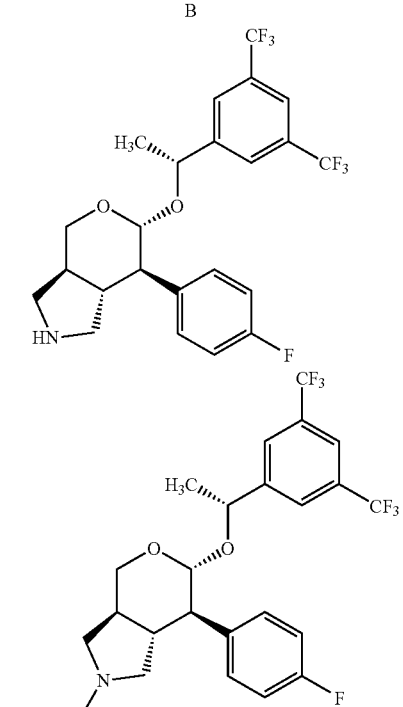
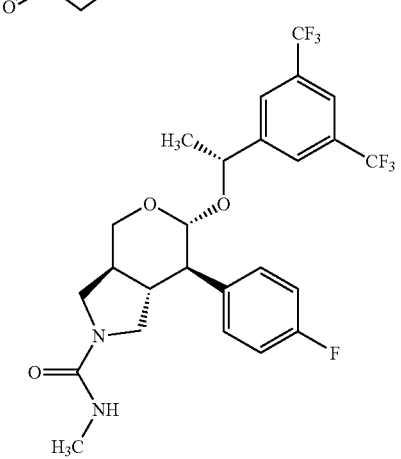

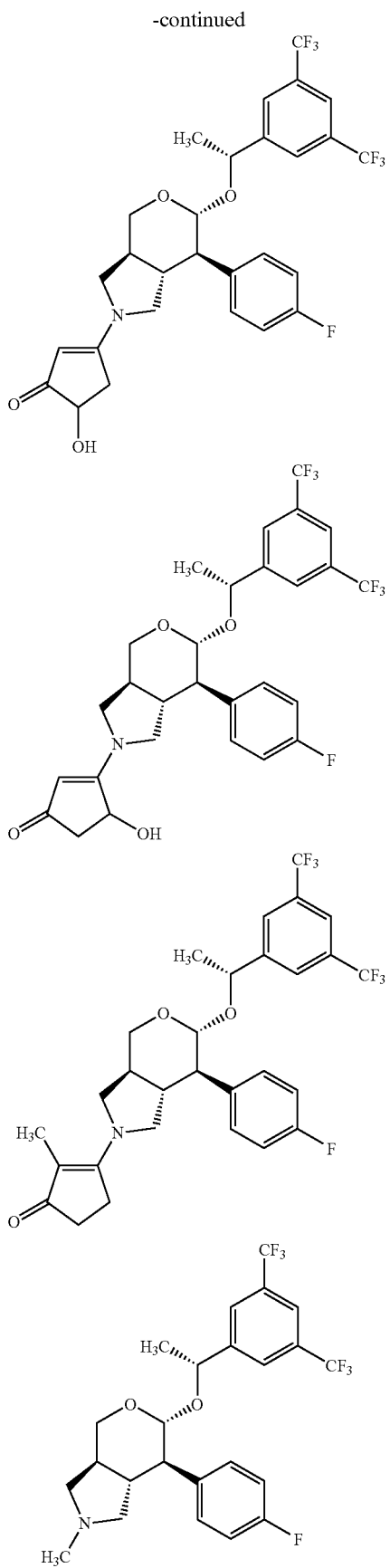
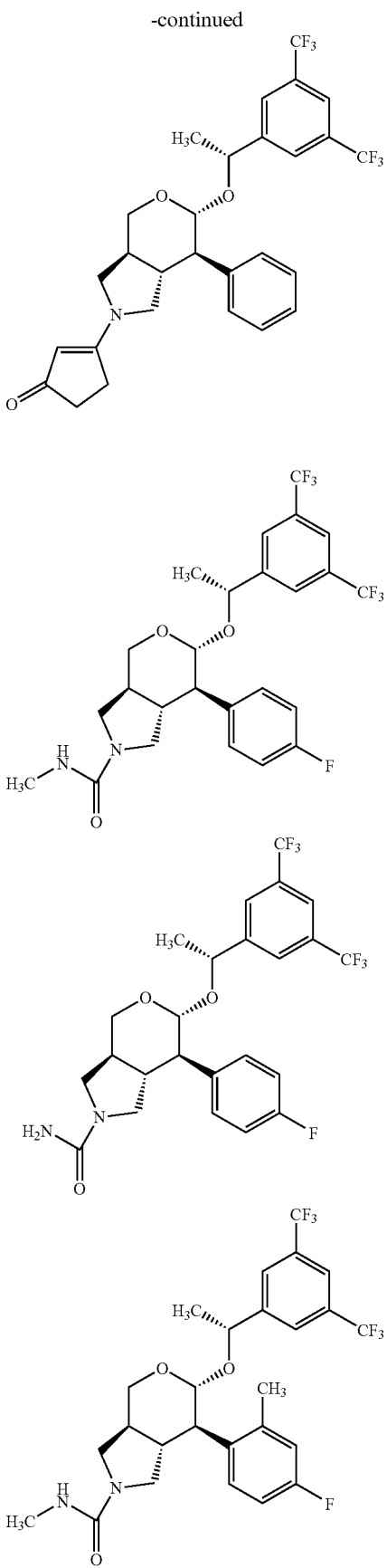

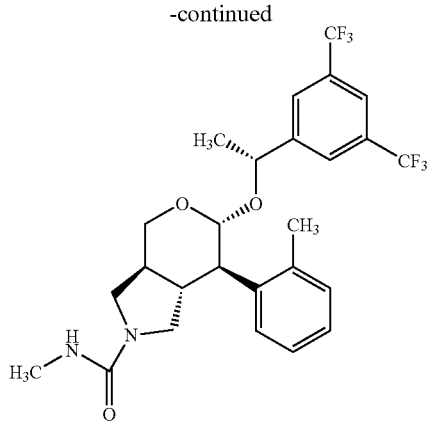
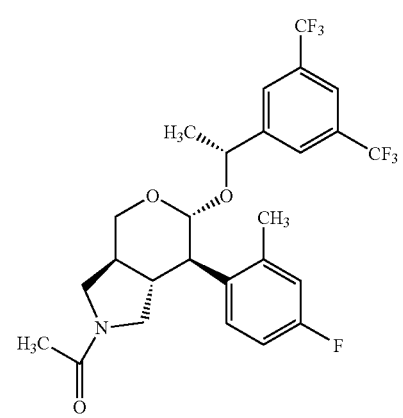
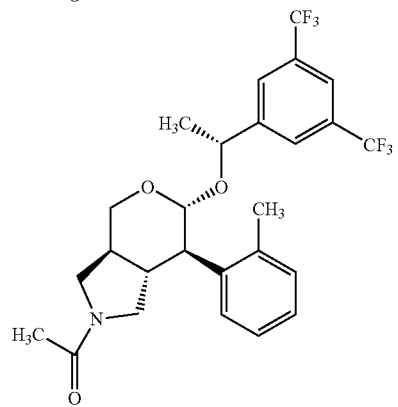
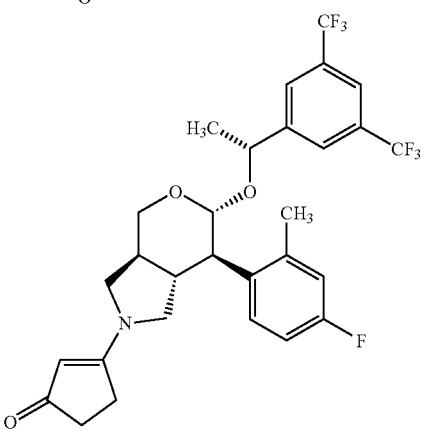
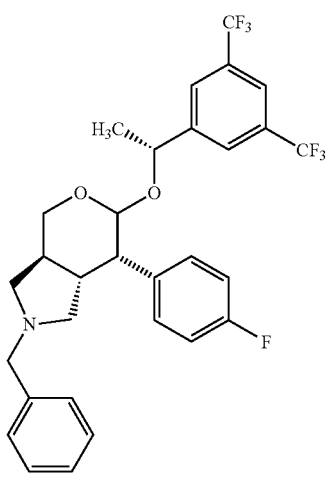
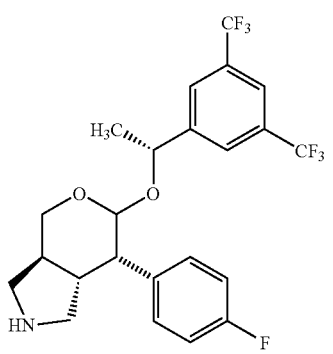
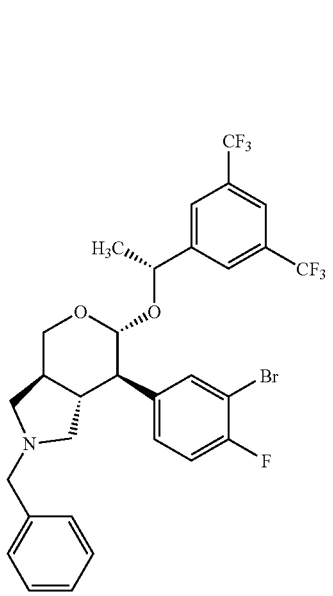
and pharmaceutically acceptable salts thereof, -continued
51
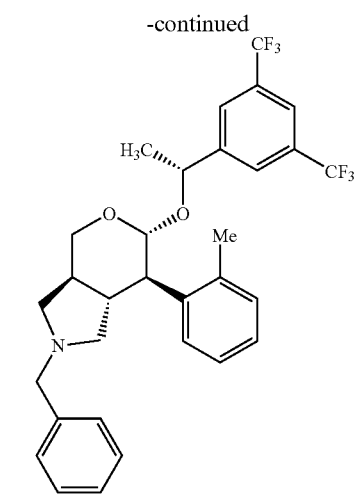
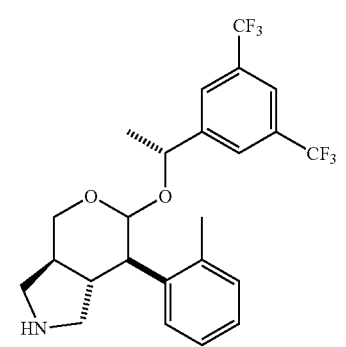
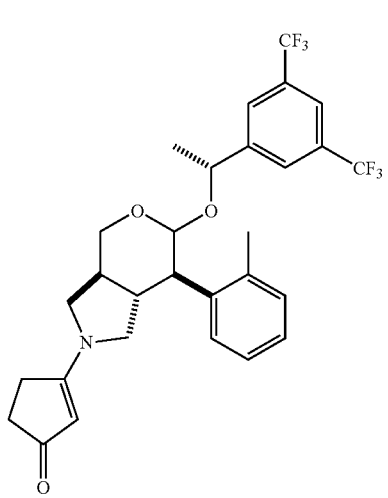
52
-continued
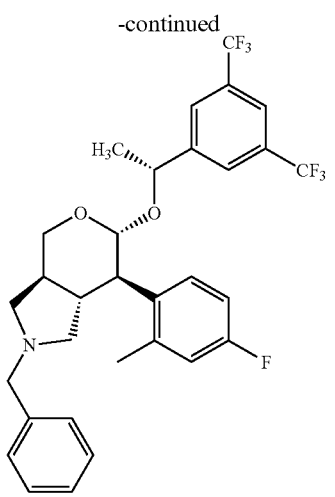
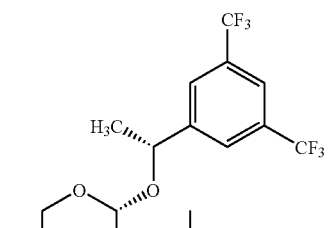
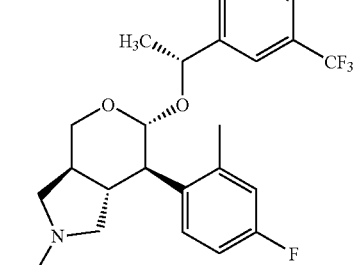
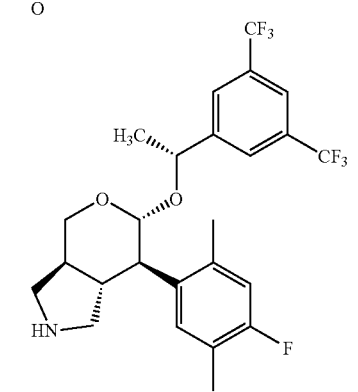

-continued
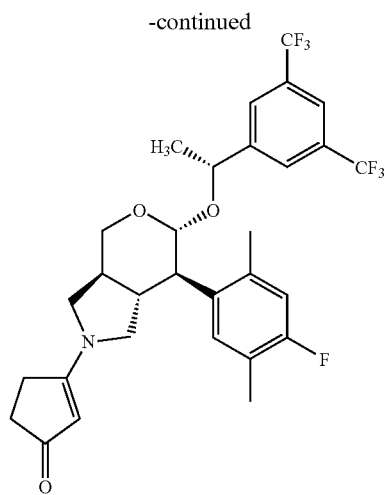
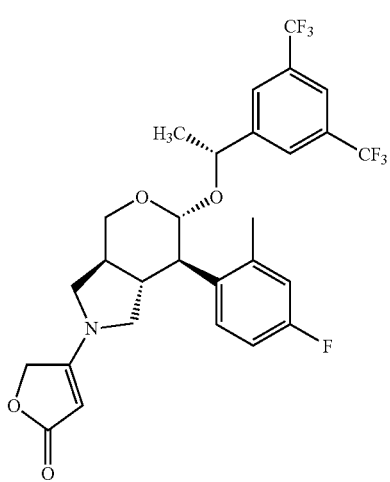
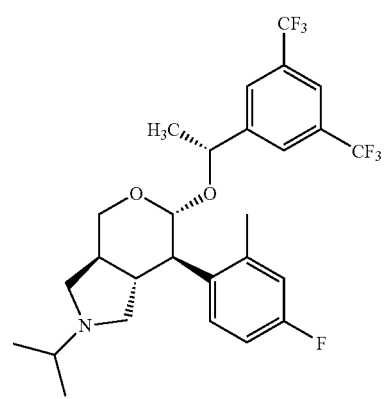
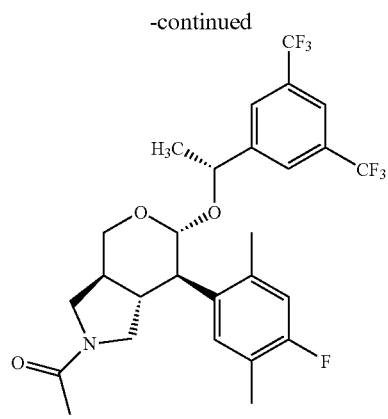
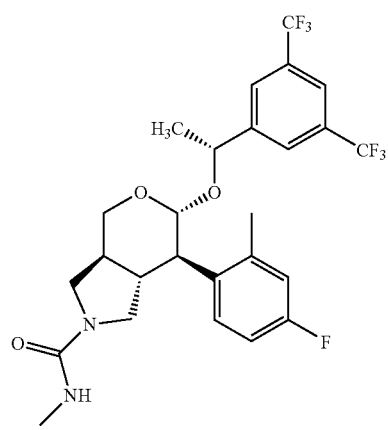
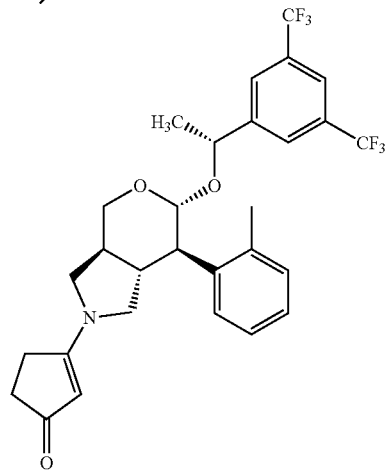
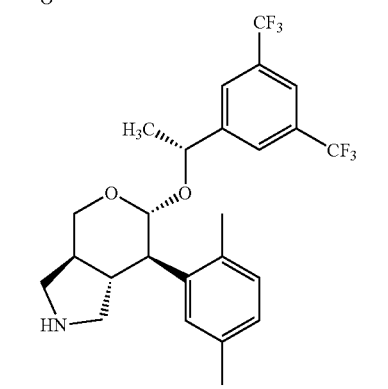

-continued
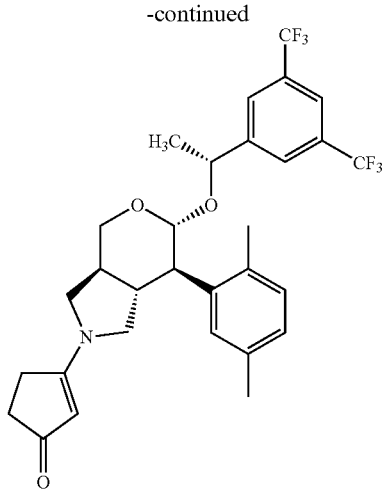
10. A compound of claim 1 of the formula
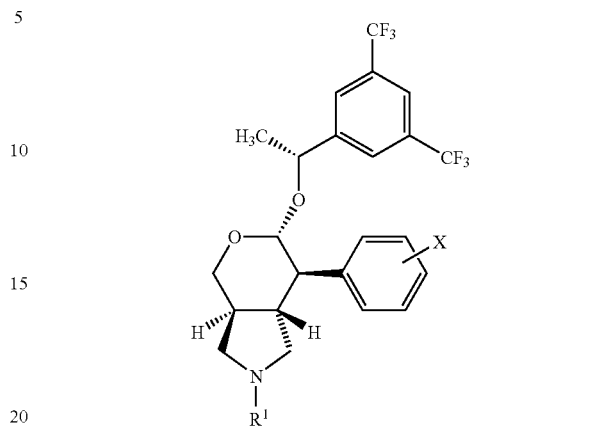
| Ex | R¹ | X |
|---|---|---|
| 28 | 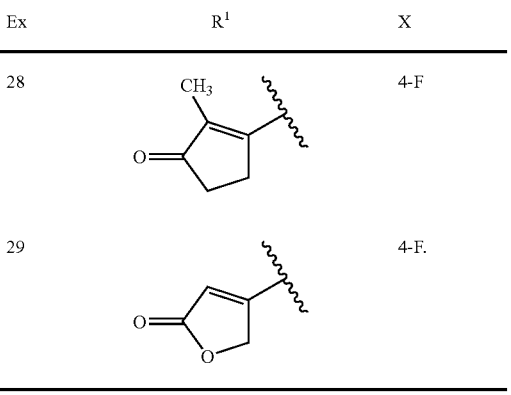 (top structure) | 4-F |
| 29 | (bottom structure) | 4-F. |
11. A compound of claim 1 of the formula
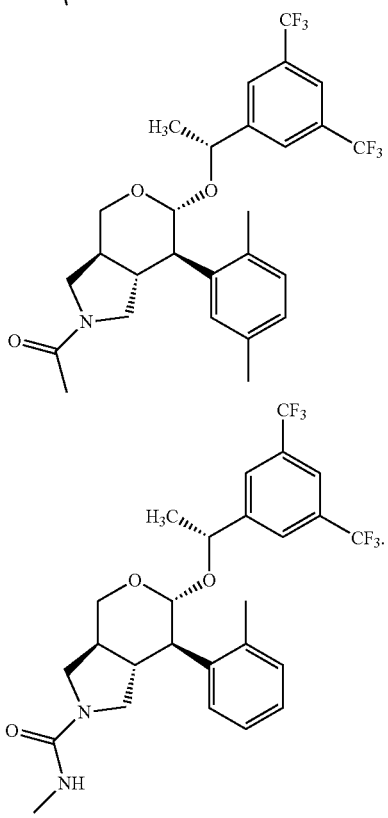
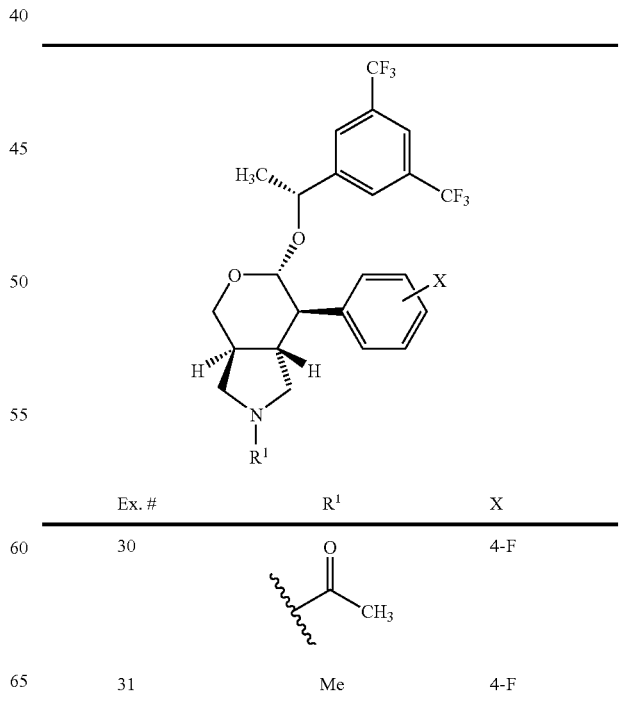
| Ex. # | R¹ | X |
|---|---|---|
| 30 |  | 4-F |
| 31 | Me | 4-F |

-continued
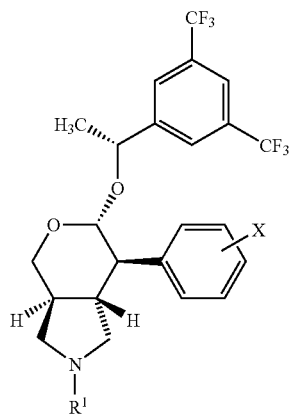
| Ex. # | R¹ | X |
|---|---|---|
| 32 | 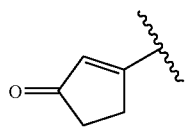 | H |
| 33 | 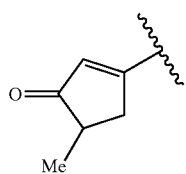 | 4-F |
| 34 | 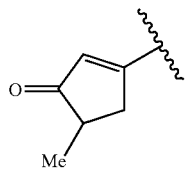 | 2-Me |
-continued
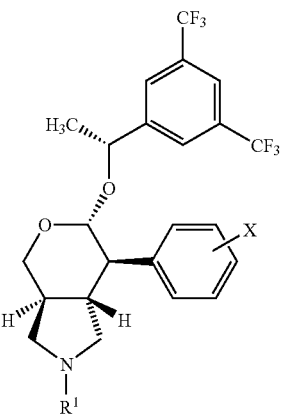
| Ex. # | R¹ | X |
|---|---|---|
| 35 | 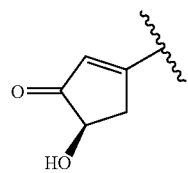 | 2-Me |
| 36 | 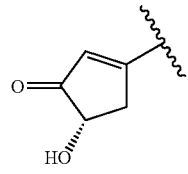 | 2-Me |
| 37 | 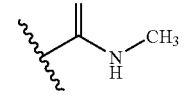 | 4-F. |
12. A pharmaceutical composition which comprises an inert carrier and a compound of claim 1 or a pharmaceutically acceptable salt thereof.
* * * * *